United States Patent [19]

Bugaut et al.

[11] 4,417,896

[45] * Nov. 29, 1983

[54] HAIR DYE COMPOSITIONS AND NEW COMPOUNDS USEFUL THEREIN

[75] Inventors: Andrée Bugaut, Boulogne-sur-Seine; Patrick Andrillon, Aulnay-sous-Bois, both of France

[73] Assignee: Societe Anonyme dite: L'Oreal, Paris, France

[ * ] Notice: The portion of the term of this patent subsequent to Jun. 29, 1999 has been disclaimed.

[21] Appl. No.: 365,993

[22] Filed: Apr. 6, 1982

Related U.S. Application Data

[63] Continuation of Ser. No. 682,798, May 3, 1976, Pat. No. 4,337,061, which is a continuation-in-part of Ser. No. 628,999, Nov. 5, 1975, abandoned.

[30] Foreign Application Priority Data

Nov. 5, 1974 [FR] France .................................. 74 36651
Apr. 3, 1976 [FR] France .................................. 76 18985

[51] Int. Cl.³ .................. A61K 7/13; C07C 93/14; C07C 79/46; C07C 103/29
[52] U.S. Cl. .................................. 8/414; 8/405; 8/407; 8/416; 560/22; 562/437; 564/47; 564/50; 564/97; 564/153; 564/156; 564/164; 564/166; 564/193; 564/284; 564/336; 564/346; 564/353; 564/354; 564/441
[58] Field of Search .................. 8/405, 407, 414, 416; 560/22; 562/437; 564/47, 50, 97, 153, 156, 166, 164, 193, 284, 336, 346, 353, 354, 441; 132/7

[56] References Cited

U.S. PATENT DOCUMENTS

| | | | |
|---|---|---|---|
| 1,669,764 | 5/1928 | Knecht | 564/441 |
| 2,518,077 | 8/1950 | Schmid et al. | 564/441 |
| 2,750,326 | 6/1956 | Eckardt | 8/415 |
| 2,750,327 | 6/1956 | Eckardt | 8/415 |
| 2,927,132 | 3/1960 | Barber et al. | 564/441 |
| 3,274,249 | 9/1966 | Brunner et al. | 8/405 X |

FOREIGN PATENT DOCUMENTS 2132214 3/1975 France .
120081 10/1918 United Kingdom .
1171104 11/1969 United Kingdom .

OTHER PUBLICATIONS

Chemical Abstracts, vol. 41, Cols. 5484–5485, (1947).

*Primary Examiner*—Natalie Trousof
*Assistant Examiner*—Vera C. Clarke
*Attorney, Agent, or Firm*—Cushman, Darby & Cushman

[57] ABSTRACT

Novel compounds of the general formula

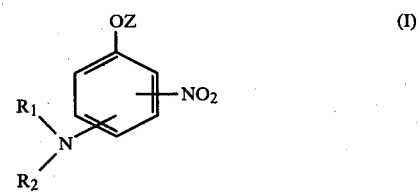

wherein Z represents a substituted lower alkyl radical; each of $R_1$ and $R_2$ is hydrogen atom, a lower alkyl or a substituted lower alkyl identical with or different from Z and the functional groups $NO_2$ and $NR_1R_2$ can occupy all ring positions in relation to OZ, with the exception that if Z is β-hydroxyethyl, $-NO_2$ is in the 4 position and $-N(R_1)(R_2)$ is in the 2 position then either $R_1$ or $R_2$ is other than hydrogen.

The novel compounds are for dyeing human hair in a variety of yellow shades. The compounds of formula (I) may be used as aqueous or water-alcohol solutions to form dye compositions for dyeing human hair.

15 Claims, No Drawings

HAIR DYE COMPOSITIONS AND NEW COMPOUNDS USEFUL THEREIN

This is a continuation, of application No. 682,798 filed May 3, 1976, now U.S. Pat. No. 4,337,061, which is a continuation-in-part of Ser. No. 628,999, filed Nov. 5, 1975, now abandoned.

The present invention relates to dyeing compositions for human hair, which contain in solution at least an etheroxide of the general formula:

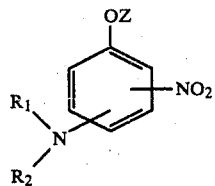

wherein Z is a substituted lower alkyl radical; each of $R_1$ and $R_2$ is hydrogen, lower alkyl, or a substituted lower alkyl identical with or different from Z; and the functional groups $NO_2$ and $NR_1R_2$ can occupy all the positions on the ring in relation to OZ.

By lower alkyl is meant alkyl groups of from 1 to 6 carbon atoms; preferably by lower alkyl is meant methyl and ethyl groups.

By substituted alkyl radical is meant, for example, hydroxyalkyl, aminoalkyl, carbamylalkyl, carboxyalkyl or carbalkoxyalkyl radicals, wherein the alkyl radical contains from 1 to 6 carbon atoms.

It has now been discovered that the properties of the compounds of general formula (I), can vary widely depending on the nature of the definition of moieties encompassed by Z in (I) above. That is, the nature of properties of (I) above can be varied by varying Z.

For instance, compounds of the state of the art in which Z is alkyl can be modified by substitution of the alkyl by a hydroxyl or carboxyl group. Substitution of that alkyl in this manner results in compounds of enhanced solubility characteristics compared to unsubstituted alkyl.

When the alkyl of Z is substituted by moieties which are basic, the corresponding compounds have an increased affinity for hair, and thus greater lasting power.

Compounds in which Z is carbamylalkyl will present less selectivity than those for which Z is alkyl, thus giving a better unison to hair partially sensitized and treated prior to dyeing.

The hair dye compositions of the invention are aqueous or water-alcohol solutions which are easily prepared by dissolving, in water or in a water-alcohol mixture, one or more compounds of formula (I). When alcohols are used in these compositions, the alcohol is present in an amount of 20 to 75% by weight of the dye composition and is preferably 25 to 50% by weight of the dye composition. The alcohols used in the dye compositions are preferably ethanol or isopropanol, although any alcohol of 1-4 carbon atoms may be used.

The concentration of the compounds of formula (I) in the dye compositions according to the invention can vary over wide limits because of their good affinity for hair. This amount of the dye (I) in these compositions is generally between 0.001 and 5% by weight, and, preferably, between 0.05 and 5% by weight of the dye composition.

The pH of the compositions according to the invention is generally between 3 and 11.5 and, preferably, between 3 and 10.5. The pH is adjusted to the desired value by addition of an acid such as phosphoric acid or lactic acid or a base such as triethanolamine or ammonia.

The compositions according to the invention can contain various adjuvants conventionally used in cosmetics, for example, wetting agents, dispersing agents, swelling agents, penetrating agents, emollients or perfumes. They can also contain solvents such as glycols and glycol esters.

The compositions according to the invention can also contain other direct dyes such as azo or anthraquinone dyes, nitro dyes of the benzene series, indoanilines, indophenols or indamines.

The compositions according to the invention can be used for lasting dyeing of hair: in this case, the compositions are applied to the hair for a period varying from 3 to 30 minutes; application is followed by rinsing, and possibly washing, and drying the hair.

The compositions according to the invention can also be used as capillary setting lotions, which lotions give the hair a slight coloring and, at the same time, improve the holding of the setting. In this case, the compositions of the invention are in the form of water-alcohol solutions containing at least one cosmetic resin. Application of capillary setting lotion is made to wet hair which has been previously washed and rinsed; after application, the hair is then rolled up and dried.

The cosmetic resins used in the composition of these setting lotions are employed in a proportion of 1 to 3% by weight, and preferably 1 to 2% by weight of the composition. Cosmetic resins which may be used include polyvinylpyrrolidone, copolymers of (1) crotonic acid-vinyl acetate, (2) vinylpyrrolidone-vinyl acetate, (3) maleic anhydride-butylvinyl ether, or (4) maleic anhydride/vinyl methyl ether and its ethyl, isopropyl and butyl esters.

The setting lotions according to the invention generally contain 20–75% by weight, and preferably 25 to 50% by weight, of a low molecular weight alcohol, which preferably is ethanol or isopropanol.

The etheroxides of formula (I) defined above are novel compounds with the exception of (4-nitro-2-amino)-phenoxyethanol already described in U.S. Pat. No. 1,669,764.

As set forth above, the present invention is also directed to the compounds of the general formula (I):

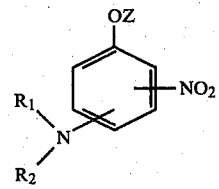

wherein Z represents a substituted lower alkyl radical, each of $R_1$ and $R_2$, identical or different, can be a hydrogen atom, a lower alkyl radical or a substituted lower alkyl radical, identical with or different from Z, and functional groups $NO_2$ and $NR_1R_2$ can occupy all positions on the ring in relation to OZ, with the exception that if and when (1) Z is β-hydroxyethyl, (2) —$NO_2$ is in the 4 position and —$NR_1R_2$ is in the 2 position then either $R_1$ or $R_2$ is other than hydrogen.

In particular, Z in formula (I) is a substituted lower alkyl and each of $R_1$ and $R_2$ is hydrogen, lower alkyl, or substituted lower alkyl. By lower alkyl is meant an alkyl of 1 to 6 carbon atoms. Preferably each of $R_1$ and $R_2$ is hydrogen, methyl or ethyl. By substituted lower alkyl is meant a lower alkyl substituted by —OH (hydroxy), —NH$_2$ (amino), —N(R$_3$)$_2$ (primary or secondary amino), —COOH or —CONH$_2$.

As set forth above, if the position of —OZ in formula (I) is arbitrarily chosen as position 1 in the ring, then either of —NO$_2$ and —NR$_1$R$_2$ may be in the 2, 3, 4, 5 or 6 position on the ring, relative to —OZ with the qualification set forth above. Generally, —NR$_1$R$_2$ may be in the 2, 4, 5 or 6 position on the ring while —NO$_2$ is in the 2, 3, 4 or 5 position; preferably —NR$_1$R$_2$ is in the 2, 3, 4 or 5 position when —NO$_2$ is the 2, 3, 4 or 5 position. The only qualification, as mentioned above, is that if Z is β-hydroxyethyl and if —NO$_2$ is in the 4 position and if —NR$_1$R$_2$ is in the 2 position, then either of $R_1$ and $R_2$ is other than hydrogen.

The compounds of formula (I) are obtained by the reaction, in DMF (dimethylformamide), of alkylating agents of the formula XZ, wherein X represents a halogen atom and Z a substituted alkyl radical, Z being as defined above, with alkaline salts (phenates) of the compounds of formula (II), wherein the molar ratio of alkylating agent to the said alkaline salt is between 1 and 11 and preferably 1.1 and 4,

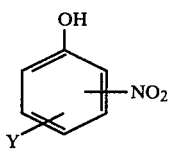 (II)

and wherein Y can be halogen (Cl, Br or F), NH$_2$,

$R_1$ and $R_2$ have the values mentioned above; NO$_2$ and Y can occupy all the positions on the ring in relation to OH, except if Y is a halogen atom, and if Y is halogen then Y is in a position ortho or para to the NO$_2$ group, with formation of the compound of formula (III)

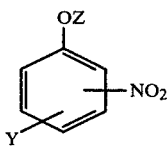 (III)

and by optional treatment of the compound III to transform the Y group into the final NR$_1$R$_2$ group. The reaction can be also carried out in HMPT(hexamethylphosphorotriamide). The reaction temperatures are in the range of 50° to 120° C. and preferably between 70° and 100° C. In the case where Y represents a halogen atom, an amine is reacted with compound (III) to produce I. Amines used in the reaction include, for example, methylamine, butylamine, ethanolamine and β-diethylaminoethylamine.

When Y is

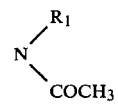

in compound (III), then compound (III) is treated with hydrochloric acid, which results in compound (I) in which $R_2$ is hydrogen. Then, such a compound (I) wherein $R_2$ is hydrogen is reacted with compound XZ to alkylate —NR$_1$R$_2$ and replace $R_2$ by a group $R_2$ other than hydrogen.

It is further possible to modify the nature of Z of the etheroxide function or of the amine function, for instance, when Z, $R_1$ or $R_2$ is a carbamylalkyl radical, treating a compound containing is radical with hydrochloric acid will result in transforming that radical to carboxyalkyl so that Z, $R_1$ or $R_2$ is transformed into a carboxyalkyl group.

XZ compounds which can be used, include e.g., glycol bromohydrin, diethylamino ethylchloride and chloracetamide.

The alkaline salts of compounds (II) can be prepared in a first stage by treating such compounds (II) with an aqueous or water-alcohol solution of potassium or sodium hydroxide. However, alkaline salts of (II) can be obtained in situ by adding potassium or sodium hydroxide directly into the dimethylformamide, i.e., used as the reaction medium in which the condensation of XZ with the alkaline salt of (II) is performed.

The compounds (II) are generally known and can be prepared in a way known per se.

Those compounds, wherein Y is halogen, have previously been prepared as follows:

2-chloro 3-nitrophenol by Meldola Eyre, JCS 81, 996;

2-nitro 5-chlorophenol by De Kewiet, Stephen JCS 1931,84;

2-nitro 3-chlorophenol by Modgson, Moore, JCS 127, 1600;

3-chloro 4-nitrophenol in the DRP 143.449;

2-bromo 5-nitrophenol by Fries Saftien, Berichte 59, 1253;

2-chloro 5-nitrophenol by Meldola Woolcott JCS 69, 1326; and 3-nitro 4-chloro phenol by Meldola Woolcott JCS 69, 1322.

Compounds wherein Y is NH$_2$, NHR$_1$,NR$_1$R$_2$, NHCOCH$_3$ or NR$_1$COCH$_3$ are disclosed in the following sublications.

2-nitro 6-amino phenols are disclosed, inter alia, in Post et Stuckenberg Annales 205 page 85 and in Berichte 1959 92 407;

3-nitro 5-amino phenols are disclosed, for example, in Compte Rendu des Travaux Chimiques des Pays Bas 27, 27 and Berichte 42 2192 (Heller Kammann);

3-nitro 4-amino phenols are disclosed, for example, in Berichte 39, 3796 Berichte 27 195; and Chem.Soc.1967 p.1053 (Amery Corbett);

2-nitro 4-amino phenols are disclosed, for example, in Berichte 27 196 and 197; JCS 105, 2077 (Meldola and Hollely) and Chem. Soc. (Amery Corbett);

2-nitro 3-amino phenols are disclosed, for example, in Chem.Soc.1967 (Amery Corbett);

2-amino 3-nitro phenols are disclosed, for example, in Chem.Ber.1959, 92, 407 (Zinner Herbig);

2-nitro 5-amino phenols are described, inter alia, in JCS 89, 925 (Meldola, Stephens); the French patent 1,063,979; and Chem. Soc. 1967 (Amery,Corbett);

2-amino 5-nitro phenols are disclosed for example, in Berichte 27 (Friedlander Zetlin); Chem.Soc.1967, p 1053 (Amery Corbett) and BP 1,012,793;

2-amino 4-nitro phenols are disclosed, inter alia, in Annales 75, 68 (Laurent Gerhardt); and Chem.Soc. 1967, p 1053 (Amery Corbett).

3-amino 4-nitro phenols are disclosed, inter alia, in JCS 89 924 (Meldolo and Stephen); and Chem.Soc.1967 p.1053 (Amery Corbett).

EXAMPLE a

Preparation of 3-nitro 6-acetylamino phenol as employed in Example 8 below:

0.51 mole (78.5 g) of 2-amino 5-nitro phenol is dissolved in 120 cc of dioxane at 80° C. Then with stirring, 0.56 mole (53.5 cc) of acetic anhydride was gradually added. When the addition is completed, heating to reflux is continued for 10 minutes; then the mixture is cooled. After crystallization 3-nitro 5-acetylamino phenol is drained and dried. It melts with decomposition above 250° C.

EXAMPLE b

Preparation of 2-nitro 5-N,N-diethylamino phenol as employed in the examples 14 and 21

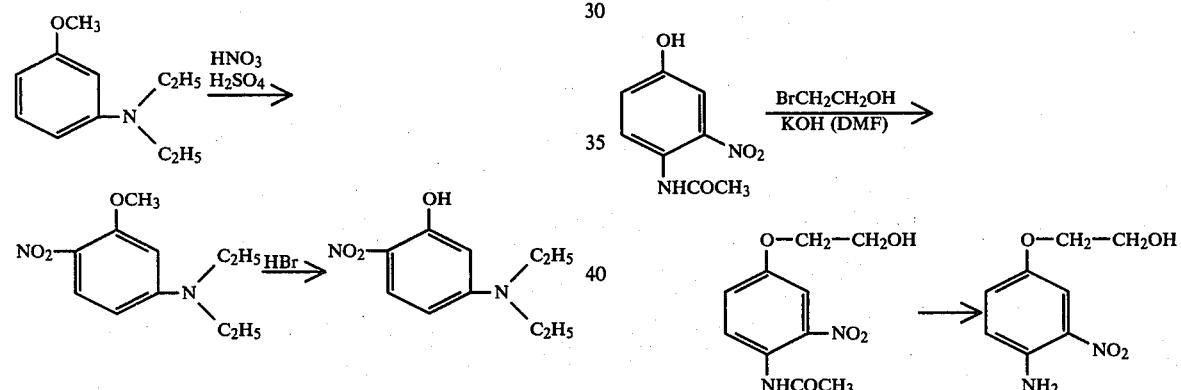

FIRST PHASE

Preparation of 3-methoxy 4-nitro N,N-diethylaniline 1 mole (179 g) of N,N-diethylmeta-anisidine was dissolved in 700 cc sulfuric acid (d=1.83). The reaction mixture is cooled at −10° C. and 96 cc of sulfonitric mixture (46 cc HNO₃ d=1.52; 50 cc H₂SO₄ d=1.83) were gradually added with stirring and while keeping the temperature between −10° and −5° C. When the addition is completed the mixture is maintained at −10° C. for 20 minutes; then it is poured over 5 kg ice. 1 liter of 10 N soda solution is gradually added. After precipitation the raw product is drained. After recrystallization in acetic acid 138 g of 3-methoxy 4-nitro N,N-diethylaniline were obtained. The product melts at 75° C.

SECOND PHASE

Preparation of 2-nitro 5-N,N-diethylamino phenol 0.61 mole (138 g) of 3-methoxy 4-nitro N,N-diethylaniline is added to 400 cc 66% hydrobromic acid. The mixture is heated to reflux for four hours and a half and cooled. To the reaction mixture are added 800 cc of water, and the expected product is drained. After recrystallization in acetic acid it melts at 110° C.

| Analysis | Calculated for $C_{10}H_{14}N_2O_3$ | Found |
|---|---|---|
| C % | 57.13 | 57.10 |
| H % | 6.71 | 6.83 |
| N % | 13.33 | 13.30 |

EXAMPLE c

Preparation of 4-nitro 2-acetylamino phenol as employed in Example 6 below:

0.2 mole (31 g) of 2-amino 4-nitro phenol is dissolved in 47 cc of dioxane at 80° C. With stirring 0.2 mole (21 cc) of acetic anhydride is added gradually. The reflux is maintained for 10 minutes. The reaction mixture is cooled, and, after crystallization 4-nitro 2-acetylamino phenol is drained. It melts with decomposition above 260° C.

The following examples illustrate the preparation of compounds and compositions of the invention, as well as the methods employed in accordance with the invention. The Examples are illustrative only and are meant to be construed as encompassing all conventional equivalents and alternatives of the art.

EXAMPLE 1

Preparation of (3-nitro-4-amino) phenoxyethanol

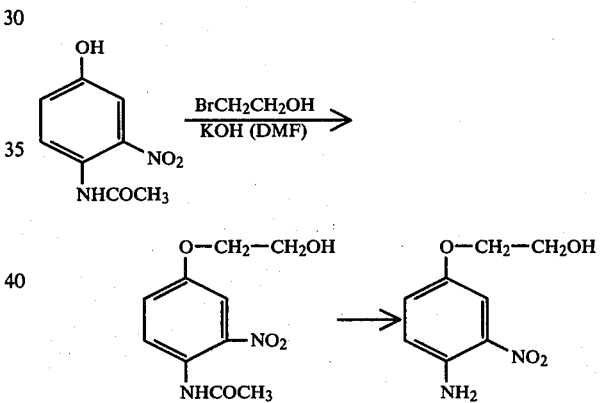

First Phase

Preparation of (3-nitro 4-acetylamino)phenoxyethanol 0.1 mole (19.6 g) of 3-nitro 4-acetylamino phenol is dissolved in 60 cc of dimethylformamide; there is then added to this solution 0.155 mole of 85% potassium hydroxide (10.2 g) in 22 cc of a dilute alcohol solution (20% water, 80% ethanol) and 0.17 mole (21.25 g) of glycol bromohydrin. At the end of two and a half hours of heating in a boiling double boiler, the reaction mixture is poured into 200 cc of ice water to which 70 g of sodium chloride are added to precipitate the (3-nitro 4-acetylamino) phenoxyethanol. The expected product is drained and dried under vacuum. After recrystallization in benzene and drying under vacuum it melts at 107° C.

| ANALYSIS | Calculated for $C_{10}H_{12}N_2O_5$ | Found |
|---|---|---|
| C % | 50.00 | 49.98 |
| H % | 5.04 | 5.13 |

-continued

| ANALYSIS | Calculated for $C_{10}H_{12}N_2O_5$ | Found |
|---|---|---|
| N % | 11.66 | 11.47 |

Second Phase

Preparation of (3-nitro 4-amino)phenoxyethanol

There is introduced 0.07 mole (17 g) of (3-nitro 4-acetylamino) phenoxyethanol in 34 cc of hydrochloric acid (d=1.18), then the reaction mixture is stirred, while maintained at boiling or reflux temperatures over a water bath, for 45 minutes. The hydrochloric solution is then cooled to −15° C. to cause the expected product to precipitate in the form of hydrochloride. The hydrochloride is separated. It is then redissolved in 60 cc of water. After neutralization with sodium acetate, the (3-nitro 4-amino)phenoxyethanol which has precipitated is separated. After recrystallization in boiling water and drying under vacuum the product melts at 117° C.

| ANALYSIS | Calculated for $C_8H_{10}N_2O_4$ | Found | |
|---|---|---|---|
| C % | 48.48 | 48.21 | 48.37 |
| H % | 5.09 | 5.12 | 5.14 |
| N % | 14.14 | 14.22 | 14.19 |

EXAMPLE 2

Preparation of (3-nitro 4-methylamino)phenoxyethanol

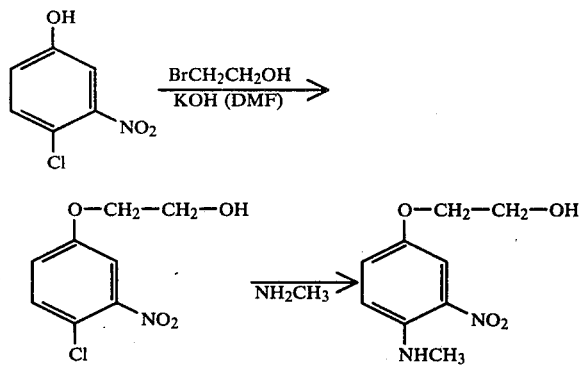

First Phase

Preparation of (3-nitro 4-chloro)phenoxyethanol 0.316 mole (55 g) of 3-nitro 4-chloro phenol is dissolved in 165 cc of dimethylformamide to which have been added 29 g of potassium hydroxide in powder form and 0.47 mole (85 g) of 70% glycol bromohydrin. The reaction mixture is heated to a temperature of about 100° C., with stirring. After two hours of heating, 7.5 g of potassium hydroxide in powder form and 0.11 mole (20 g) of 70% glycol bromohydrin are added to the mixture. The heating is again continued for two hours and again 5 g of potassium hydroxide in powder form and 0.08 mole (12 g) of 70% glycol bromohydrin are added. After two new hours of heating, the reaction mixture, after cooling is poured into 800 cc of ice water. The desired product which precipitates is isolated. It is washed with water, then with a normal soda solution to eliminate traces of 3-nitro 4-chloro phenol, then again with water. After recrystallization in a 50% water-ethanol mixture and drying under vacuum the product melts at 96° C.

| ANALYSIS | Calculated for $C_8H_8O_4NCl$ | Found |
|---|---|---|
| C % | 44.30 | 44.22 |
| H % | 3.72 | 3.86 |
| N % | 6.46 | 6.68 |
| Cl % | 16.35 | 16.30 |

Second Phase

Preparation of (3-nitro 4-methylamino)phenoxyethanol 0.0092 mole (2 g) of (3-nitro 4-chloro) phenoxyethanol and 15 g of 40% aqueous solution of methylamine are heated in a sealed tube at 60° C. for 24 hours. After cooling of the reaction mixture, the (3-nitro 4-methylamino)phenoxyethanol, which has crystallized, is separated from the solution. The product is washed with water, made to recrystallize in boiling water and dried under vacuum. It melts at 113° C.

| ANALYSIS | Calculated for $C_9H_{12}O_4N_2$ | Found |
|---|---|---|
| C % | 50.94 | 50.65 |
| H % | 5.70 | 5.81 |
| N % | 13.20 | 13.44 |

EXAMPLE 3

Preparation of (3-nitro 2-amino) phenoxyethanol

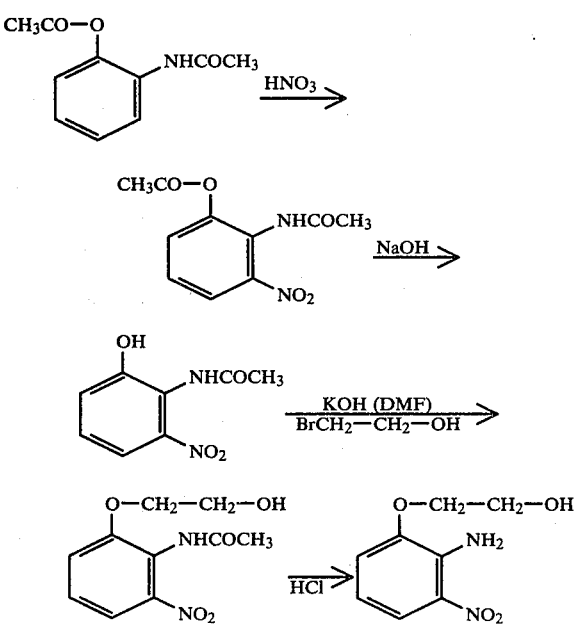

First Phase

Preparation of 2-acetylamino 3-nitro phenol 36 cc of nitric acid (d=1.52) are gradually added to a suspension of 0.66 mole (128 g) of 2-acetoxy acetanilide in 400 cc of acetic anhydride, with stirring, while maintaining the temperature at about 35° C.

When the addition is finished, the reaction mixture is cooled to 0° C.; then the raw product, which has recrystallized (95 g) is washed with water. This product is a mixture of 2-acetoxy 6-nitro acetanilide and 2-acetoxy 4-nitro acetanilide. The raw product is introduced, with stirring, into 230 cc of a 4 N sodium hydroxide solution. The reaction mixture is cooled to 0° C. then 2-acetylamino 3-nitro phenol, in the form of sodium phenate, is isolated. By neutralization of the basic filtrate with acetic acid, the 2-acetylamino 3-nitro phenol is precipitated The product is drained, washed with water and dried under vacuum. It is chromatographically pure and melts at 181° C.

| ANALYSIS | Calculated for $C_8H_8N_2O_4$ | Found |
|---|---|---|
| C % | 48.98 | 49.16 |
| H % | 4.11 | 4.22 |
| N % | 14.28 | 14.12 |

Second Phase

Preparation of (3-nitro 2-acetylamino)phenoxyethanol.

0.05 mole (9.8 g) of 2-acetylamino 3-nitro phenol and 3.25 g of potassium hydroxide, previously ground are added with stirring to 50 cc of dimethylformamide cooled in an ice bath. When the dissolution is completed, the reaction mixture is heated to a temperature of about 90° C., and 0.08 mole (10 g) of bromohydrin of anhydrous glycol is gradually added with stirring. When the addition is finished, the reaction mixture is again kept for two hours at 90° C. then poured into 120 cc of ice water. Sodium chloride is added in an amount sufficient to cause the (3-nitro 2-acetylamino)phenoxyethanol to precipitate. After being left in the refrigerator for 12 hours, the desired product is drained, washed with a little ice water. After recrystallization in ethyl acetate and drying under vacuum the product melts at 162° C.

| ANALYSIS | Calculated for $C_{10}H_{12}N_2O_5$ | Found |
|---|---|---|
| C % | 50.00 | 49.78 |
| H % | 5.04 | 5.20 |
| N % | 11.66 | 11.51 |

Third Phase

Preparation of (3-nitro 2-amino)phenoxyethanol 0.029 mole (7.0 g) of (3-nitro 2-acetylamino)phenoxyethanol is added to 15 cc of hydrochloric acid (d=1.18); then the reaction mixture is heated for an hour at about 90° C. Then the reaction mixture is poured into 75 cc of ice water. The (3-nitro 2-amino)phenoxyethanol precipitates. The product is drained, washed with water and recrystallized in ethyl acetate. After drying under vacuum the product melts at 146° C.

| ANALYSIS | Calculated for $C_8H_{10}N_2O_4$ | Found |
|---|---|---|
| C % | 48.48 | 48.40 |
| H % | 5.09 | 5.19 |
| N % | 14.14 | 14.26 |

EXAMPLE 4

Preparation of (2-nitro 4-amino)phenoxyethanol

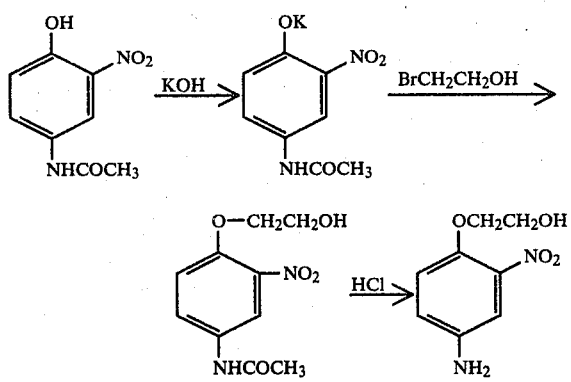

First Phase

Preparation of potassium salt of 2-nitro 4-acetylamino phenol 0.7 mole (40 g) of potassium hydroxide in pellets is dissolved in 120 cc of water-ethanol solution (80% ethanol, 20% water). To this potassium salt solution is added gradually, with stirring, and while keeping the temperature between 0° and 5° C., 0.3 mole (59 g) of 2-nitro 4-acetylamino phenol. When the addition is finished, the stirring is continued for some minutes; then the potassium salt of the 2-nitro 4-acetylamino phenol is isolated.

Second Phase

Preparation of (2-nitro 4-acetylamino)phenoxyethanol 0.3 mole (70 g) of the potassium salt of 2-nitro 4-acetylamino phenol is added to 150 cc of dimethylformamide; then there is added, with stirring, 0.5 mole (35 cc) of bromohydrin of anhydrous glycol. The reaction mixture is heated for two and a half hours at a temperature of about 100° C., then poured into 350 cc of ice water. The raw (2-nitro 4-acetylamino)phenoxyethanol precipitates. The raw product is drained, washed with water then with a normal soda solution to eliminate the 2-nitro 4-acetylamino phenol which has not reacted and finally with water. After recrystallization in acetic acid and drying under vacuum the product melts at 173° C.

| ANALYSIS | Calculated for $C_{10}H_{12}N_2O_5$ | Found |
|---|---|---|
| C % | 50.00 | 50.19 |
| H % | 5.04 | 5.12 |
| N % | 11.66 | 11.82 |

Third Phase

Preparation of (2-nitro 4-amino)phenoxyethanol 0.133 mole (32 g) of (2-nitro 4-acetylamino)pheoxyethanol is added to 40 cc of hydrochloric acid (d=1.18). Then this reaction mixture is heated for about an hour at a temperature of about 100° C. The hydrochloric solution is then cooled to −15° C. to precipitate, in crystalized form, the chlorhydrate of (2-nitro 4-amino)-phenoxyethanol. The chlorhydrate is drained, washed with a little iced hydrochloric acid (d=1.18), then dried under vacuum.

| Molecular mass | |
|---|---|
| calculated for $C_8H_{11}O_4N_2Cl$ | 234.5 |
| found by potentiometric dosing | 231 |

The chlorhydrate previously obtained (26 g) with stirring is introduced into 250 cc of ammonia water to obtain (2-nitro 4-amino)phenoxyethanol. The dye is drained, washed with water and dried under vacuum. It melts at 91° C.

| ANALYSIS | Calculated for $C_8H_{10}N_2O_4$ | Found |
|---|---|---|
| C % | 48.48 | 48.25 |
| H % | 5.09 | 5.07 |
| N % | 14.14 | 14.07 |

EXAMPLE 5

Preparation of (2-nitro 4-N-methylamino)phenoxyethanol in hydrochloride form

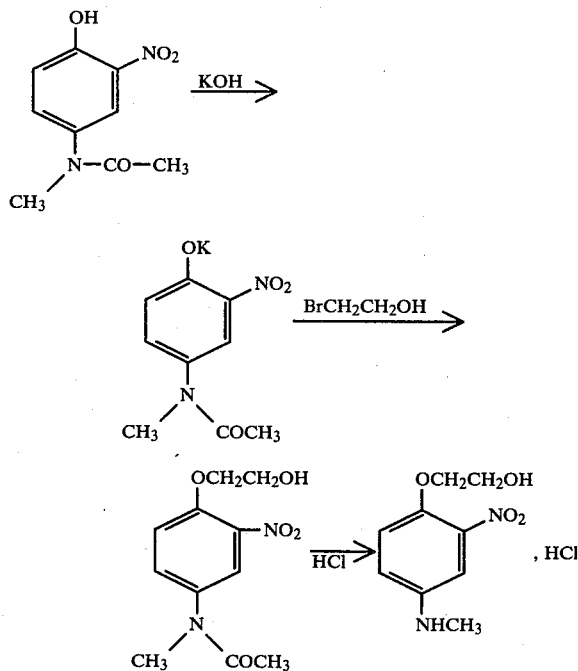

First Phase

Preparation of potassium salt of 2-nitro N-methyl 4-acetylamino phenol 0.5 mole (28 g) of potassium hydroxide is dissolved in 145 cc of water-ethanol solution (85% ethanol, 15% water). To this potassium salt solution is added 0.26 mole (55 g) of 2-nitro 4-N-methylacetylamino phenol gradually, with stirring and while maintaining the temperature between 0° and 5° C. When the addition is completed, the stirring is continued for some minutes then the potassium salt of 2-nitro 4-N-methylacetylamino phenol is drained washed with a little alcohol and dried.

Second Phase

Preparation of (2-nitro 4-N-methylacetylamino)phenoxyethanol 34.75 g (0.14 mole) of potassium salt of 2-nitro 4-N-methylacetylamino phenol are introduced into 105 cc of dimethylformamide then 10 cc (0.15 mole) of bromohydrin of anhydrous glycol. The reaction mixture is heated for about two hours at about 100° C. and then poured into 250 cc of ice water. Sodium chloride is added to cause the expected nitro derivative to precipitate. The product is isolated by filtration, washed with a little ice water and is then recrystallized in ethyl acetate. After drying under vacuum the product melts at 135° C.

| ANALYSIS | Calculated for $C_{11}H_{14}N_2O_5$ | Found |
|---|---|---|
| C % | 51.96 | 51.78 |
| H % | 5.55 | 5.67 |
| N % | 11.02 | 11.15 |

Third Phase

Preparation of (2-nitro 4-N-methylamino)phenoxyethanol hydrochloride 0.094 mole (24 g) of (2-nitro 4-N-methylacetylamino)-phenoxyethanol is introduced into 35 cc of hydrochloric acid (d=1.18). Then the reaction mixture is heated in a water bath for three hours. The mixture is then filtered hot; and the filtrate is cooled to 0° C. to cause the (2-nitro 4-N-methylamino)phenoxyethanol to precipitate in crystallized form, which melts with decomposition at 155° C.

| ANALYSIS | Calculated for $C_9H_{13}N_2O_4Cl$ | Found |
|---|---|---|
| C % | 43.46 | 43.26 |
| H % | 5.23 | 5.47 |
| N % | 11.27 | 11.20 |
| Cl % | 14.25 | 14.37 |

EXAMPLE 6

Preparation of (4-nitro 2-amino)phenoxyethanol

-continued

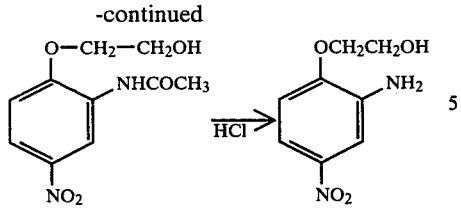

First Phase

Preparation of sodium salt of 4-nitro 2-acetylamino phenol

0.6 mole (118 g) of 4-nitro 2-acetylamino phenol is dissolved in 800 cc of normal sodium solution. To this solution 500 cc of 10 N sodium solution are added to cause the sodium phenate to precipitate. The product is filtered, washed twice with 100 cc of ethanol and dried.

Second Phase

Preparation of (4-nitro 2-acetylamino)phenoxyethanol

0.335 mole (73 g) of sodium salt of 4-nitro 2-acetylamino phenol is added to 360 cc of dimethylformamide, to which mixture is then added, with stirring, 0.4 mole (50 g) of bromohydrin of anhydrous glycol. The reaction mixture is heated for two hours at about 100° C., filtered, then poured into two liters of ice water. The (4-nitro 2-acetylamino)phenoxyethanol precipitates. The raw product is drained, washed with water then with a normal sodium solution to eliminate the 4-nitro 2-acetylamino phenol that has not reacted, then with water, and then dried under vacuum. It melts at 178° C.

Third Phase

Preparation of (4-nitro 2-amino)phenoxyethanol

0.0514 mole (10 g) of (4-nitro 2-acetylamino)phenoxyethanol is added to 40 cc of hydrochloric acid (d=1.18). Then the reaction mixture is maintained for one hour at 0° C.

The hydrochloric solution is then cooled to −15° C. to precipitate, in crystallized form, the 4-nitro 2-amino phenoxyethanol hydrochloride. The hydrochloride is filtered, washed with a little ice hydrochloric acid (d=1.18) then with acetone and dried under vacuum.

The hydrochloride previously obtained (8.2 g) is dissolved in 75 cc of water. Ammonia is added, with stirring, to neutralize the aqueous solution and thus to precipitate the 4-nitro 2-aminophenoxyethanol. The product is drained, washed with water and dried under vacuum. It melts at 105° C.

| ANALYSIS | Calculated for $C_8H_{12}N_2O_4$ | Found | |
|---|---|---|---|
| C % | 48.48 | 48.31 | 48.57 |
| H % | 5.09 | 4.99 | 5.12 |
| N % | 14.14 | 14.08 | 13.98 |

EXAMPLE 7

Preparation of (4-nitro 2-β-hydroxyethylamino)phenoxyethanol

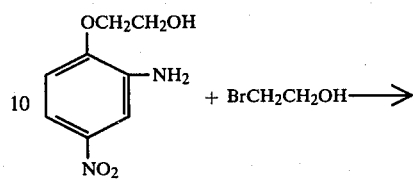

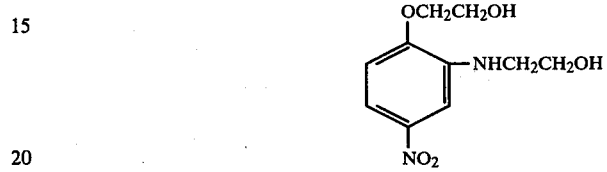

0.01 mole (2.345 g) of (4-nitro 2-amino)phenoxyethanol hydrochloride is added to 12 cc of water to which has been added 0.016 mole (1.6 g) of calcium carbonate. The mixture is heated to about 100° C. Then there is added gradually, with stirring, 0.02 mole (3.6 g) of 70% glycol bromohydrin. When the addition is completed, the heating is continued for two and a half hours at 100° C. Then the hot reaction medium is filtered. The filtrate is cooled to cause the (4-nitro 2-β-hydroxyethylamino)phenoxyethanol to precipitate in crystallized form. The product is drained, washed with a little water and made to recrystallize in ethanol. After drying under vacuum, the product melts at 143° C.

| ANALYSIS | Calculated for $C_{10}H_{14}O_5N_2$ | Found | |
|---|---|---|---|
| C % | 49.58 | 49.60 | 49.35 |
| H % | 5.83 | 5.98 | 5.88 |
| N % | 11.57 | 11.76 | 11.58 |

EXAMPLE 8

Preparation of (3-nitro 6-amino) phenoxyethanol

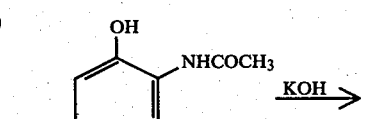

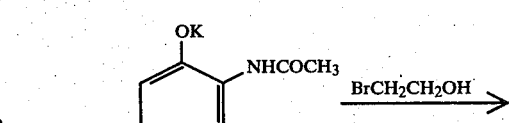

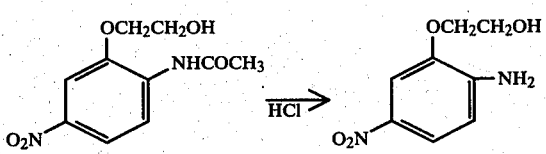

First Phase

Preparation of potassium salt of 3-nitro 6-acetylamino phenol

2.28 moles (150 g) of potassium hydroxide in pellet form are dissolved in 150 cc of water then 975 cc of ethanol are added. To this water-alcohol solution are gradually added, with stirring and while maintaining the temperature between 0° and 5° C., 1.5 moles of 3-nitro 6-acetylamino phenol (294 g). When the addition is completed, stirring is continued for 15 minutes; then the potassium salt of 3-nitro 6-acetylamino phenol is filtered.

Second Phase

Preparation of (3-nitro 6-acetylamino)phenoxyethanol

0.5 mole (117 g) of potassium salt of 3-nitro 6-acetylamino phenol is added to 600 cc of dimethylformamide; then, with stirring, 0.6 mole (75 g) of bromohydrin of anhydrous glycol is added to the dimethylformamide mixture. The reaction mixture is then heated for an hour and a half in a water bath, and then poured, after cooling, into three liters of ice water. The raw (3-nitro 6-acetylamino)phenoxyethanol precipitates. The raw product is filtered, washed with water, then washed with a normal sodium solution to eliminate a little of the original 3-nitro 6-acetylamino phenol and again washed with water. After recrystallization in acetic acid and drying under vacuum, the product melts at 168° C.

| ANALYSIS | Calculated for $C_{10}H_{12}O_5N_2$ | Found | |
|---|---|---|---|
| C % | 50.00 | 50.26 | 50.21 |
| H % | 5.04 | 5.14 | 5.17 |
| N % | 11.66 | 11.43 | 11.47 |

Third Phase

Preparation of (3-nitro 6-amino)phenoxyethanol

A mixture of 0.635 mole (152.5 g) of (3-nitro 6-acetylamino)phenoxyethanol and 600 cc of hydrochloric acid (d=1.18) is prepared; then the reaction medium is heated an hour and a half in a boiling water bath. The hydrochloric solution is then cooled with an ice-salt mixture to precipitate, in crystalized form, the (3-nitro 6-amino) phenoxyethanol hydrochloride. The hydrochloride is drained, washed with a little hydrochloric acid, and then washed with acetone. The product is chromatographically pure. The hydrochloride previously obtained is introduced with stirring into a liter of ammonia water to obtain (3-nitro 6-amino) phenoxyethanol. The dye is drained, washed with water and dried under vacuum. It melts at 143° C.

| ANALYSIS | Calculated for $C_8H_{10}O_4N_2$ | Found | |
|---|---|---|---|
| C % | 48.48 | 48.20 | 48.27 |
| H % | 5.09 | 5.28 | 5.15 |
| N % | 14.14 | 14.02 | 14.21 |

EXAMPLE 9

Preparation of (3-nitro 6-β-hydroxyethylamino)phenoxyethanol

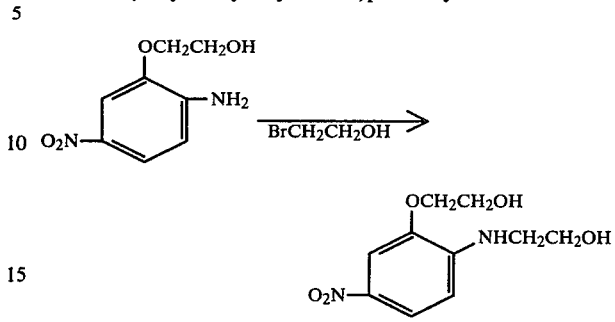

0.268 mole (63 g) of (3-nitro 6-amino)phenoxyethanol hydrochloride is added to 200 cc of water to which has been added 0.9 mole (90 g) of calcium carbonate. The mixture is heated to about 100° C.; then, with stirring, 1.5 moles (270 g) of 70% glycol bromohydrin are gradually added. After 3 hours heating in a boiling water bath, 0.36 mole (36 g) of calcium carbonate is added, and then gradually 0.6 mole (108 g) of 70% glycol bromohydrin is added. After two additional hours of heating in the boiling water bath, there are again added 0.12 mole (12 g) of calcium carbonate and 0.2 mole (36 g) of 70% glycol bromohydrin. Heating in the boiling water bath is continued for two more hours; then the reaction medium is filtered hot to eliminate the mineral salts. It is then cooled to 0° C. to precipitate (3-nitro 6-β-hydroxyethylamino)phenoxyethanol in crystallized form. The product is filtered, washed with a little water, recrystallized in a 50% water-ethanol mixture and dried under vacuum. It melts at 144° C.

| ANALYSIS | Calculated for $C_{10}H_{14}N_2O_5$ | Found | |
|---|---|---|---|
| C % | 49.58 | 49.59 | 49.54 |
| H % | 5.83 | 6.09 | 6.05 |
| N % | 11.57 | 11.39 | 11.58 |

EXAMPLE 10

Preparation of (3-nitro 6-carbamylmethylamino)phenoxyethanol

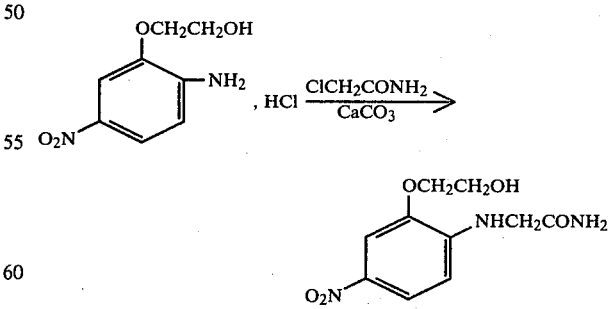

0.05 mole (11.73 g) of (3-nitro 6-amino)phenoxyethanol hydrochloride is added to 60 cc of water to which have been added 0.12 mole (12 g) of calcium carbonate and 0.26 mole (24.4 g) of chloracetamide. Then the mixture is brought to reflux with stirring. After four hours heating, 0.06 mole (6 g) of calcium carbonate and 0.13 mole (12.2 g) of chloracetamide are added. The boiling reaction medium is maintained at reflux temperatures for 6 hours before being filtered to eliminate the mineral salts. The filtrate is cooled at 0° C. over night to cause the (3-nitro 6-carbamylmethylamino)phenoxyethanol to precipitate in crystallized form. The product is filtered, washed with a little ice water and dried under vacuum. It melts at 190° C.

| ANALYSIS | Calculated for $C_{10}H_{13}N_3O_5$ | Found |
|---|---|---|
| C % | 47.06 | 46.88 |
| H % | 5.13 | 5.22 |
| N % | 16.47 | 16.47 |

EXAMPLE 11

Preparation of (3-nitro 6-carboxymethylamino)phenoxyethanol

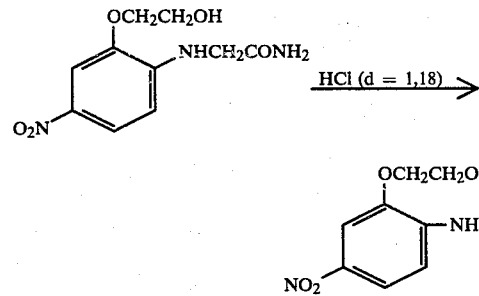

0.0039 mole (1 g) of (3-nitro 6-carbamylmethylamino)phenoxyethanol is added to 4 cc of hydrochloric acid (d=1.18). The hydrochloric solution is kept at 100° C. for an hour. Then 5 cc of cold water are added to cause the desired (3-nitro 6-carboxymethylamino)phenoxyethanol to precipitate. The product is filtered, washed with a little cold water and recrystallized in acetonitrile. After drying under vacuum at 50° C. it melts with decomposition at 195° C.

| Molecular mass | |
|---|---|
| Calculated for $C_{10}H_{12}N_2O_6$ | 256 |
| Found by potentiometric determination with a titrated sodium solution | 259 |

| ANALYSIS | Calculated for $C_{10}H_{12}N_2O_6$ | Found |
|---|---|---|
| C % | 46.88 | 46.60 |
| H % | 4.72 | 4.86 |
| N % | 10.93 | 11.07 |

EXAMPLE 12

Preparation of (3-nitro 6-β-diethylaminoethylamino)phenoxyethanol

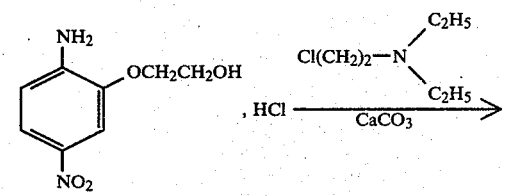

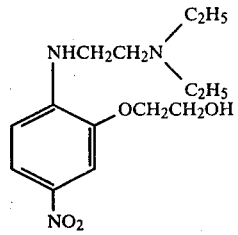

0.035 mole (8.2 g) of (3-nitro 6-amino)phenoxyethanol hydrochloride is added to 80 cc of water to which have been added 7 g of calcium carbonate. The mixture is brought to reflux with stirring; then 0.07 mole (12.1 g) of diethylaminoethylchloride hydrochloride is gradually added. After 20 hours of reflux the reaction mixture is cooled. Then the (3-nitro 6-β-diethylaminoethylamino)phenoxyethanol hydrochloride which has precipitated is filtered. This hydrochloride is partially dissolved in 100 cc of hot water. To the resulting suspension is added, gradually, with stirring a 4 N sodium hydroxide solution to attain a pH of 9. After cooling of the sodium solution, the expected product is drained, washed with water and dried under vacuum. It melts at 69° C.

| ANALYSIS | Calculated for $C_{14}H_{23}N_3O_4$ | Found |
|---|---|---|
| C % | 56.55 | 56.25 |
| H % | 7.80 | 7.50 |
| N % | 14.13 | 13.92 |

EXAMPLE 13

Preparation (2-nitro 5-N-methylamino)phenoxyethanol

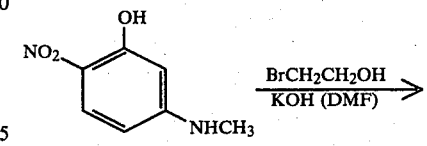

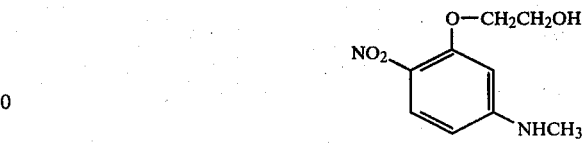

0.03 mole (5 g) of 2-nitro 5-N-methylamino phenol is dissolved in 20 cc of dimethylformamide. Then to this solution 0.03 mole of 85% potassium hydroxide (1.90 g) and 0.03 mole (2.1 cc) of anhydrous glycol bromohydrin are added. The reaction medium is heated in a boiling water bath for 10 hours while four times, every two hours, 0.03 mole of potassium hydroxide and 0.03 mole of glycol bromohydrin are added. After cooling, the reaction mixture is poured into 100 cc of iced normal sodium hydroxide solution. The resulting sodium salt solution is extracted with methylisobutylketone. The solvent is driven off under vacuum. The oily residue (3 g) rapidly crystallizes. After recrystallization in ethyl acetate and drying under vacuum, it melts at 110° C.

| ANALYSIS | Calculated for C$_9$H$_{12}$N$_2$O$_4$ | Found |
|---|---|---|
| C % | 50.94 | 51.14 |
| H % | 5.70 | 5.50 |
| N % | 13.20 | 13.44 |

EXAMPLE 14

Preparation of (2-nitro 5-N,N-diethylamino)phenoxyethanol monohydrate

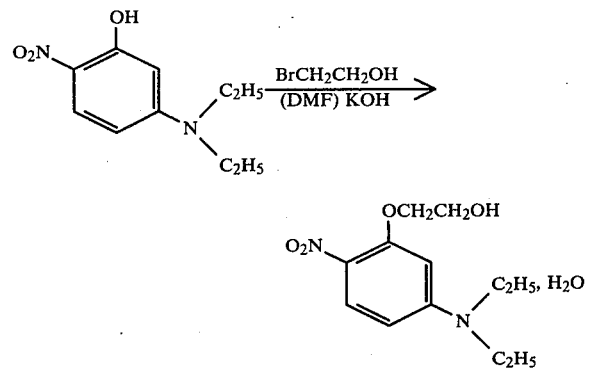

0.02 mole (4.2 g) of 2-nitro 5-N,N-diethylamino phenol is dissolved in 20 cc of dimethylformamide. Then to this solution 0.04 mole (2.6 g) of 85% potassium hydroxide and 0.04 mole of anhydrous glycol bromohydrin (2.8 cc) are added. The reaction medium is heated for 8 hours in a boiling water bath while 3 times, every two hours, 0.04 mole of potassium hydroxide and 0.04 mole of glycol bromohydrin are added. After cooling, it is poured into 200 cc of iced normal sodium hydroxide solution. The desired product precipitates in crystallized form. It is filtered, washed with water and dried in the air. It melts at 38° C.

| ANALYSIS | Calculated for C$_{12}$H$_{18}$N$_2$O$_4$(H$_2$O) | Found |
|---|---|---|
| C % | 52.93 | 52.83 |
| H % | 7.40 | 7.00 |
| N % | 10.29 | 10.29 |

EXAMPLE 15

Preparation of hydrochloride of (3-nitro-6-amino) phenyl β-N,N-diethylaminoethyl ether

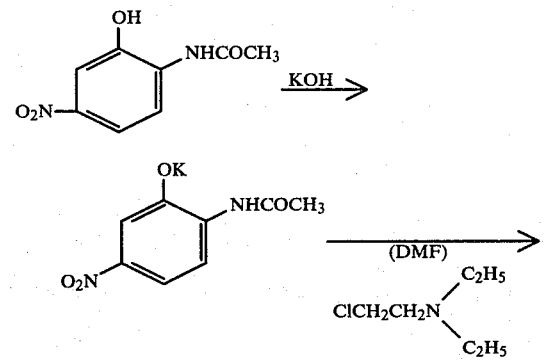

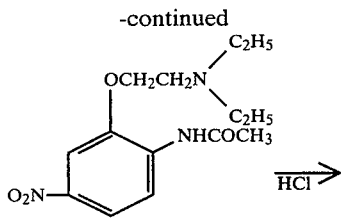

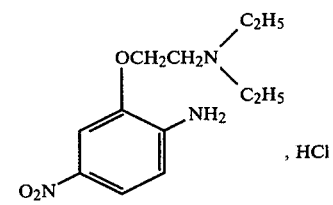

First Phase

Preparation of potassium salt of 3-nitro 6-acetylamino phenol 0.3 mole (20 g) of 85% potassium hydroxide is dissolved in 150 cc of water-ethanol solution (85% ethanol, 15% water). To this potassium salt solution is added 0.2 mole (39.2 g) of 3-nitro 6-acetylamino phenol gradually, with stirring and while keeping the temperature between 0° and 5° C. When the addition is completed, the phenate that has precipitated is filtered, washed with a little ethanol and dried under vacuum.

Second Phase

Preparation of (3-nitro-6-acetylamino)phenyl, β-N,N-diethylaminoethyl ether 0.05 mole (11.7 g) of potassium salt of 3-nitro 6-acetylamino phenol is dissolved in 45 cc of dimethylformamide at 80° C. There is rapidly added 0.055 mole (7.45 g) of N,N-diethylaminoethylchloride and the reaction medium is kept for 30 minutes in a boiling water bath. After cooling, the solution is poured over 130 g of ground ice to cause the desired product to precipitate. The raw product is drained, washed with water, dried and recrystallized in a benzene-cyclohexane mixture. It melts at 73° C.

| ANALYSIS | Calculated for C$_{14}$H$_{21}$N$_3$O$_4$ | Found |
|---|---|---|
| C % | 56.93 | 56.95 |
| H % | 7.17 | 7.16 |
| N % | 14.23 | 14.24 |

Third Phase

Preparation of (3-nitro 6-amino)phenyl β-N,N-diethylaminoethylether hydrochloride 0.0101 mole (3 g) of (3-nitro 6-acetylamino)phenyl β-N,N-diethylaminoethyl is introduced into 6 cc of hydrochloric acid (d=1.18). Then the reaction medium is heated for an hour and a half in a boiling water bath. There are added 5 cc of water, then a 5 N sodium hydroxide solution is added to bring the pH of the solution to 2, while cooling at 0° C. The expected hydrochloride precipitates. The product is filtered, washed with a slight amount of ice water and dried under vacuum. It melts with decomposition at 200° C.

This hydrochloride is dissolved in water. Ammonia solution at 22° Be is added to precipitate the (3-nitro 6-amino) phenyl-β-N,N-diethylaminoethylether. The product is drained, washed with water and dried under vacuum. It melts at 50° C.

| ANALYSIS | Calculated for C₁₂H₁₉N₃O₃ | Found |
|---|---|---|
| C % | 56.90 | 56.77 |
| H % | 7.56 | 7.44 |
| N % | 16.59 | 16.50 |

EXAMPLE 16

Preparation of 3-nitro 4-amino phenyl,β-N,N-diethylaminoethylether

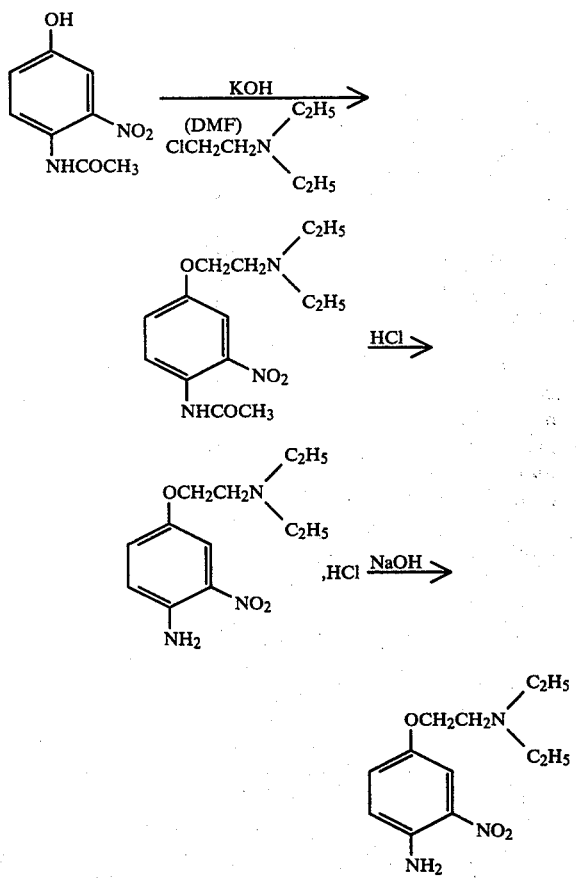

First Phase

Preparation of (3-nitro 4-acetylamino)phenyl,β-N,N-diethylaminoethylether

To a solution of 0.05 mole (9.8 g) of 3-nitro 4-acetylamino phenol in 30 cc of dimethylformamide there is added 0.055 mole (3.5 g) of 85% potassium hydroxide. To that reaction medium previously heated in the boiling water bath there is added 0.055 mole (7.45 g) of diethylaminoethylchloride. The heating is continued for an hour. After cooling of the reaction mixture, it is poured over 150 cc of ice water. An oily product precipitates. It is extracted with methylisobutylketone. The methylisobutylketone solvent is removed by evaporating under vacuum. The residue is redissolved in 40 cc of isopropanol. This solution is saturated with dry hydrochloric acid. The expected product precipitates in the form of crystallized hydrochloride. This hydrochloride is filtered, washed with a little isopropanol and dried under vacuum. It melts with decomposition at 160° C.

Second Phase

Preparation of (3-nitro 4-amino)phenyl β-N,N-diethylaminoethylether 0.121 mole (4 g) of (3-nitro 4-acetylamino)phenyl β-N,N-diethylaminoethylether is added to 8 cc of hydrochloric acid (d=1.18). Then the reaction medium is heated in a boiling water bath for two hours. After diluting with water, the hydrochloric solution is rendered basic with a sodium hydroxide solution. After cooling at 0° C. the (3-nitro 4-amino)phenyl-β-N,N-diethylaminoethylether which was first precipitated in the form of an oil crystallizes. The product is filtered, washed with water, dried then recrystallized with cyclohexane. It melts at 50° C.

| ANALYSIS | Calculated for C₁₂H₁₉N₃O₃ | Found |
|---|---|---|
| C % | 56.90 | 57.10 |
| H % | 7.56 | 7.40 |
| N % | 16.59 | 16.43 |

EXAMPLE 17

Preparation of (3-nitro 4-amino)phenyl-carbamylmethylether

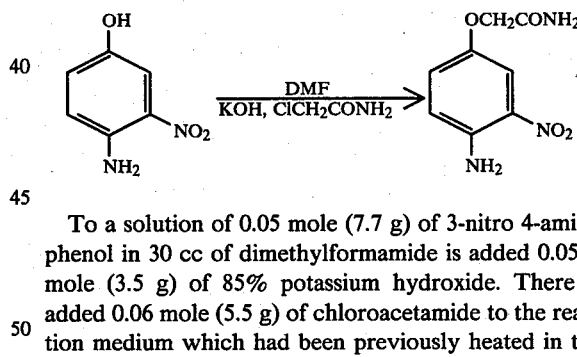

To a solution of 0.05 mole (7.7 g) of 3-nitro 4-amino phenol in 30 cc of dimethylformamide is added 0.0525 mole (3.5 g) of 85% potassium hydroxide. There is added 0.06 mole (5.5 g) of chloroacetamide to the reaction medium which had been previously heated in the boiling water bath. The heating is continued for two hours. There are then added 0.15 mole (1 g) of potassium hydroxide and 0.015 mole (1.38 g) of chloracetamide. The heating is continued for an hour more. Then the reaction medium is poured into 100 cc of ice water. The expected product precipitates. The isolated precipitate is washed with water then alcohol. After recrystallization in acetic acid the product melts at 200° C.

| ANALYSIS | Calculated for C₈H₉N₃O₄ | Found |
|---|---|---|
| C % | 45.49 | 45.50 |
| H % | 4.26 | 4.48 |
| N % | 19.90 | 20.06 |

EXAMPLE 18

Preparation of (3-nitro 4-amino)phenyl carboxymethylether.

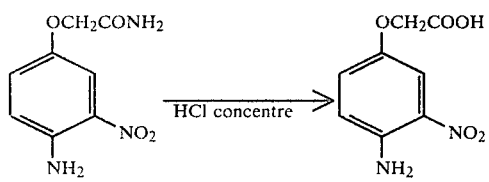

0.0142 mole (3 g) of (3-nitro 4-amino)phenyl carbamylmethylether is added to 12 cc of hydrochloric acid (d=1.19). Then the reaction mixture is heated, with stirring, for an hour in the boiling water bath. After cooling the desired product, crystallized in hydrochloride form, is filtered. This hydrochloride is dissolved in a 2.5% solution of sodium bicarbonate. Hydrochloric acid is added to effect complete precipitation of the (3-nitro 4-amino)phenyl-carboxymethylether. The product is filtered, washed with water, recrystallized in acetic acid and dried under vacuum. It melts at 188° C.

| ANALYSIS | Calculated for $C_8H_8N_2O_5$ | Found |
|---|---|---|
| C % | 45.29 | 45.01 |
| H % | 3.80 | 3.70 |
| N % | 13.21 | 13.16 |

EXAMPLE 19

Preparation of (4-nitro 5-N-methylamine)phenyl-carbamylmethylether

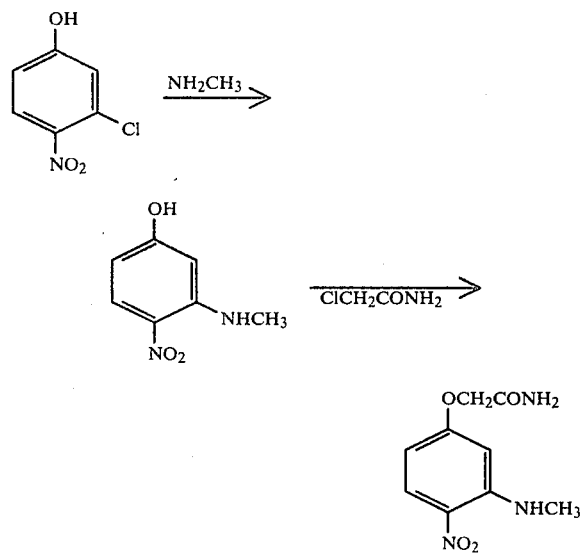

First Phase

Preparation of 4-nitro 5-N-methylamino phenol 0.052 mole (9 g) of 3-chloro 4-nitro phenol is added to 90 cc of an aqueous solution of 40% monomethylamine. This solution is kept at 60° C. and then evaporated dry under vacuum. To the residue, 30 cc of hydrochloric acid (d=1.19) are added. The 4-nitro 5-N-methyl amino phenol hydrochloride is drained and washed with acetone to eliminate any reactant remaining.

The hydrochloride (8.5 g) is treated with stirring with 50 cc of water to which has been added 1 cc of ammonia at 22° Be to release the 4-nitro 5-N-methylamino phenol. The product is filtered, washed with water, recrystallized in 30 cc of ethanol and dried under vacuum. It melts at 207° C.

| ANALYSIS | Calculated for $C_7H_8N_2O_3$ | Found |
|---|---|---|
| C % | 50.00 | 50.05 |
| H % | 4.80 | 5.10 |
| N % | 16.66 | 16.91 |

Second Phase

Preparation of (4-nitro 5-N-methylamino) phenyl carbamylmethylether

To a solution of 0.25 mole (42 g) of 4-nitro 5-N-methylamino phenol in 165 cc of dimethylformamide is added 0.3 mole (19.8 g) of 85% potassium hydroxide. 0.3 mole (28.05 g) of chloracetamide is added to the reaction medium which has been previously heated in the boiling water bath. The heating is continued for three hours. Then, 0.2 mole (13.2 g) of potassium hydroxide and 0.2 mole (18.7 g) of chloracetamide are added. The heating is continued for two more hours. Then the reaction medium is poured into 400 cc of ice water to precipitate the desired raw product. This product is filtered carefully, washed with a normal sodium hydroxide solution to eliminate any traces of the original reactant. The product is then washed with water, recrystallized in acetic acid and dried under vacuum. It melts at 213° C.

| ANALYSIS | Calculated for $C_9H_{11}N_3O_4$ | Found |
|---|---|---|
| C % | 48.00 | 48.06 |
| H % | 4.92 | 4.93 |
| N % | 18.66 | 18.60 |

EXAMPLE 20

Preparation of (4-nitro 5N-methylamino)phenyl carboxymethylether

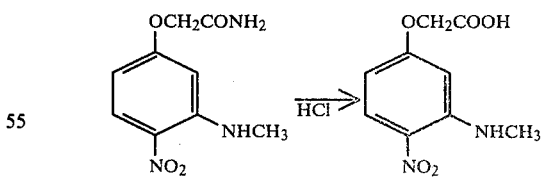

0.120 mole (27 g) of (4-nitro 5-N-methylamino)phenyl carbamylmethylether is introduced into 81 cc of hydrochloric acid (d=1.19). Then the reaction mixture is heated, with stirring, for an hour in a boiling water bath. After cooling, the (4-nitro 5-N-methylamino)phenyl-carboxymethyl ether hydrochloride is filtered and washed with a little iced hydrochloric acid. This hydrochloride is dissolved in ammonia water. Then the resulting solution is acidified to pH=4 with hydrochloric acid. The desired product precipitates. It is filtered, washed with water, recrystallized in acetic acid and dried under vacuum. It melts at 201° C.

| ANALYSIS | Calculated for $C_9H_{10}N_2O_5$ | Found |
|---|---|---|
| C % | 47.79 | 47.50 |
| H % | 4.46 | 4.73 |
| N % | 12.39 | 12.39 |

EXAMPLE 21

Preparation of (2-nitro 5-N,N-diethylamino)phenyl,β-carbamylmethylether, monohydrate

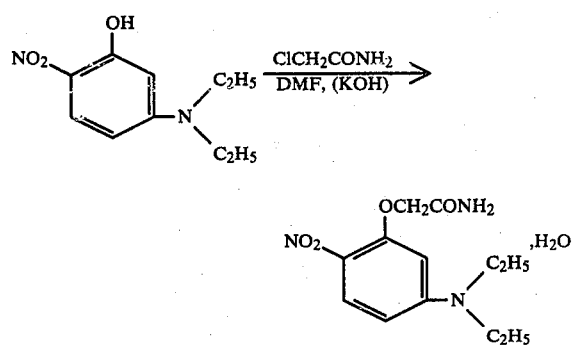

To a solution of 0.12 mole (25 g) of 2-nitro 5-N,N-diethylamino phenol in 125 cc of dimethylformamide are added 0.12 mole (7.9 g) of 85% potassium hydroxide and 0.12 mole (11.22 g) of chloracetamide. The reaction medium is heated in a boiling water bath for eight hours, while adding 3 times, every two hours, 0.12 mole of potassium hydroxide and 0.12 mole of chloracetamide. The reaction mixture is poured, after cooling, into 500 cc of an iced normal sodium hydroxide solution. The expected product precipitates in crystallized form. It is filtered, washed with water, recrystallized in ethanol and dried in the air. It melts at 193° C.

| ANALYSIS | Calculated for $C_{12}H_{17}N_3O_4, H_2O$ | Found |
|---|---|---|
| C % | 50.52 | 50.41 |
| H % | 6.71 | 6.30 |
| N % | 14.73 | 14.96 |

EXAMPLE 22

Preparation of (2-nitro, 5-N,N-diethylamino)phenyl,β-carboxymethylether

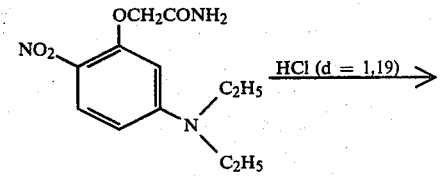

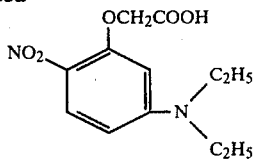

0.03 mole (8.55 g) of (2-nitro 5-N,N-diethylamino) phenyl,β-carbamylmethylether monohydrate is added to 30 cc of hydrochloric acid (d=1.19). Then the reaction mixture is heated, with stirring, for an hour and a half in a boiling water bath. After cooling, the hydrochloric solution is poured into 100 cc of ice water. Ammonia is added to adjust the solution to a pH=4 to precipitate the product. The product is filtered, washed with water, recrystallized in acetic acid and dried under vacuum. It melts at 116° C.

| ANALYSIS | Calculated for $C_{12}H_{16}N_2O_5$ | Found |
|---|---|---|
| C % | 53.72 | 53.51 |
| H % | 6.01 | 6.23 |
| N % | 10.44 | 10.51 |

EXAMPLE 23

Preparation of (5-nitro 2-carbamylethylamino)phenoxyethanol

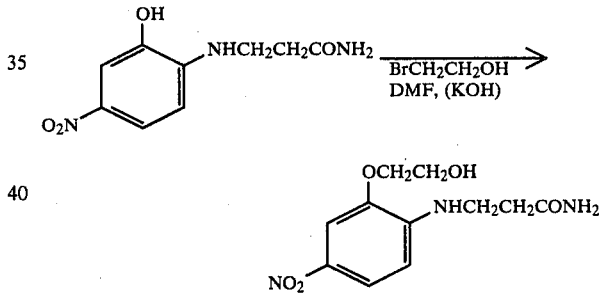

0.0088 mole (2 g) of 5-nitro, 2-carbamylethylaminophenol is dissolved in 10 cc of dimethylformamide. To this solution, are added 0.05 mole (3.5 cc) of glycol bromohydrin and 0.05 mole (3.2 g) of 85% potassium hydroxide in 5 cc of water-alcohol solution (20% water, 80% alcohol). The mixture is heated in a boiling water bath for an hour and a half. Again, 0.05 mole (3.5 cc) of glycol bromohydrin and 0.05 mole of potassium hydroxide are added to the mixture. The heating is continued for another hour. The reaction mixture is then poured into 100 cc of ice water to cause the product to precipitate. The product is filtered, washed with water, and then washed with a normal sodium hydroxide solution. After washing with water and recrystallization in alcohol, the product melts at 184° C.

| ANALYSIS | Calculated for $C_{11}H_{15}N_3O_5$ | Found |
|---|---|---|
| C % | 49.07 | 48.98 |
| H % | 5.62 | 5.71 |
| N % | 15.61 | 15.39 |

EXAMPLE 24

Preparation of (5-nitro 2-carboxyethylamino)phenoxyethanol

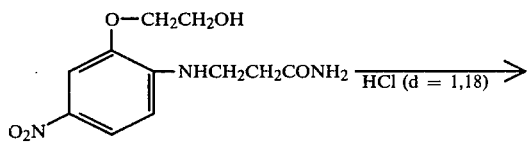

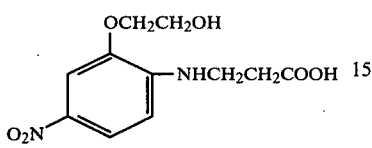

0.01 mole (2.7 g) of (5-nitro 2-carbamylethylamino) phenoxyethanol in 15 cc of hydrochloric acid (d=1.18) is heated for an hour and a half in a boiling water bath. The reaction mixture is poured into 100 cc of ice water to precipitate the product. To purify this raw product it is dissolved in a 2.5% sodium bicarbonate solution. It is filtered to eliminate an insoluble substance. Then the (5-nitro 2-carboxyethylamino) phenoxyethanol is re-precipitated by addition of acetic acid. The product is filtered, washed with water and dried. It melts at 178° C.

| ANALYSIS | Calculated for $C_{11}H_{14}N_2O_6$ | Found |
|---|---|---|
| C % | 48.89 | 49.00 |
| H % | 5.22 | 5.33 |
| N % | 10.37 | 10.24 |

EXAMPLE 25

Preparation of (2-nitro, 4-N,N-di β-hydroxyethylamino)phenoxyethanol

The following mixture including 0.0085, mole (2 g) of (2-nitro 4-amino)phenoxyethanol hydrochloride, 0.018 mole (2 cc) of 70% glycol bromohydrin in 20 cc of water to which has been added 0.02 mole (2 g) of calcium carbonate, is heated in a boiling water bath. After heating for an hour, 0.018 mole of glycol bromohydrin and 0.02 mole (2 g) of calcium carbonate are added to the mixture. The mixture is heated for an hour more in the boiling water bath. Then the hot reaction mixture is filtered. After cooling, it is extracted with ethyl acetate. The ethyl acetate is evaporated under vacuum. The oily residue slowly crystallizes in the refrigerator. After recrystallization in ethyl acetate, it melts at 88° C.

| ANALYSIS | Calculated for $C_{12}H_{18}N_2O_6$ | Found |
|---|---|---|
| C % | 50.34 | 50.13 |
| H % | 6.34 | 6.51 |
| N % | 9.79 | 9.74 |

EXAMPLE 26

Preparation of (4-nitro 5-N-methylamino) phenoxy-ethanol 0.02 mole (3:36 g) of 4-nitro 5-N-methylaminophenol described in the first part of Example 19 is dissolved in 10 cc of dimethylformamide and then 0.03 mole (2 g) of 85% potassium hydroxide and 0.03 mole (5.4 g) of 70% glycol bromohydrin are added. After heating for 3 hours on a boiling water bath, the reaction mixture is poured onto 50 g of ice. The product is drained and then dried. After recrystallization in acetic acid and drying in vacuo, the product melts at 132° C.

| ANALYSIS | Calculated for $C_9H_{12}N_2O_4$ | FOUND |
|---|---|---|
| C % | 50.94 | 50.82 |
| H % | 5.66 | 5.82 |
| N % | 13.21 | 13.25 |

EXAMPLE 27

Preparation of (3-nitro 4-amino) phenyl-carbamylmethylether

This example describes a variant of the preparation as disclosed in the example 17.

To a solution of 0.05 mole (7.7 g) of 3-nitro 4-amino phenol in 20 cc of hexamethylphosphorotriamide and 10 cc of acetone is added 0.06 mole (8.3 g) of potassium carbonate. The reaction medium is heated at 70° C. and 0.06 mole (5.6 g) of chloracetamide is added. The heating at 70° C. is continued for an hour and a half. There are then added 0.015 mole (2.07 g) of potassium carbonate and 0.015 mole (1.38 g) of chloracetamide. The heating is continued for 30 minutes more. Then the reaction medium is poured into 100 cc of ice water. The product precipitates. It is drained, washed with water. The expected product metls at 200° C.

EXAMPLE 28

Preparation of (3-nitro 4-amino) phenylcarbethoxymethyleter

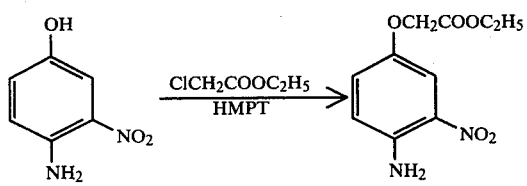

To a solution of 0.04 mole (6.16 g) of 3-nitro 4-amino phenol in 40 cc of hexamethylphosphorotriamide, is added 0.044 mole (6.07 g) of potassium carbonate. The medium is heated at 75° C. and thereto is added 0.044 mole (4.64 cc) of ethyl chloroacetate. After heating at 75° C. for an hour, 0.044 mole (6.07 g) of potassium carbonate and 0.044 mole (4.64 cc) of ethyl chloroacetate are added. The heating is continued for an hour more; then the reaction medium is poured into 150 cc ice water. The product precipitates. It is drained and washed with water. After drying the product melts at 112° C.

Use of dyeing compositions containing the compounds of formula (I), produced as above, is illustrated by the following examples which present particular embodiments of the compositions of the invention. The following examples are illustrative only and are meant to be construed as encompassing equivalents and alternatives known to the art.

EXAMPLE I

The following dye composition is prepared:

| | |
|---|---|
| Dye of example 1 | 0.5 g |
| Lauric alcohol oxyethylened with 10.5 moles of ethylene oxide | 5 g |
| Butylglycol | 5 g |
| Triethanolamine q.s.p. | pH 9 |
| Water q.s.p. | 100 g |

This dye composition is applied to 95% naturally white hair for 20 minutes at ambient temperature. After rinsing and shampooing, the hair is characterized by a saffron yellow coloring.

EXAMPLE II

The following dye composition is prepared:

| | |
|---|---|
| Dye of example 3 | 0.40 g |
| Carboxymethylcellulose | 5 g |
| Water q.s.p. | 100 g |
| Ammonia at 22° Be q.s.p. | pH 8 |

This composition, applied for 20 minutes at 35° C. to bleached hair, gives the hair, after rinsing and shampooing, a jonquil coloring.

EXAMPLE III

The operation of example 1 is followed with the following dye composition:

| | |
|---|---|
| Dye of example 6 in hydrochloride form | 0.3 g |
| Diethylene glycol monoethyl ether | 10 g |
| Water q.s.p. | 100 g |
| 20% triethanolamine q.s.p. | pH = 7 |

This dye composition, applied for 20 minutes at 30° C., to 95% naturally white hair, gives the hair after rinsing and shampooing, a canary yellow coloring.

EXAMPLE IV

The following dye solution is prepared:

| | |
|---|---|
| Dye of example 6 in hydrochloride form | 4 g |
| Sodium lauryl sulfate with 19% starting oxyethylened alcohol | 20 g |
| Trilon B (ethylenediaminetetraacetic acid) | 0.2 g |
| Ammonia at 22° Be | 10 g |
| Water q.s.p. | 100 g |

This dye composition is applied for 5 minutes at 15° C. to bleached hair. After rinsing and shampooing, the hair has a sulfur yellow coloring.

EXAMPLE V

The operation of example 1 is followed with the following dye composition:

| | |
|---|---|
| Dye of example 4 in hydrochloride form | 5 g |
| Diethanolamides of copra fatty acids | 10 g |
| Water q.s.p. | 100 g |
| Ammonia q.s.p. | pH = 10 |

This dye composition is applied to 95% naturally white hair for 20 minutes at ambient temperature. After rinsing and shampooing, the hair is of a golden yellow coloring.

EXAMPLE VI

The following dye composition is prepared:

| | |
|---|---|
| Dye of example 8 | 0.4 g |
| Carboxymethylcellulose | 5 g |
| Water q.s.p. | 100 g |
| 5% lactic acid solution q.s.p. | pH = 4 |

This dye composition is applied to 95% naturally white hair for 10 minutes at ambient temperature. After rinsing and shampooing, the hair has a greenish-yellow coloring.

EXAMPLE VII

The following dye composition is prepared:

| | |
|---|---|
| Dye of example 8 | 0.1 g |
| 96° ethyl alcohol | 25 g |
| Ammonia at 22° Be q.s.p. | pH = 9 |
| Water q.s.p. | 100 g |

This composition, applied for 20 minutes at 20° C. to 95% naturally white hair, gives it, after rinsing and shampooing, an absinth yellow coloring.

EXAMPLE VIII

The following dye composition is prepared:

| | |
|---|---|
| Dye of example 2 | 0.5 g |
| Lauric alcohol reacted with 10.5 moles of ethylene | 5 g |

-continued

| | |
|---|---|
| oxide | |
| Water q.s.p. | 100 g |
| Ammonia at 22° Be q.s.p. | pH 10 |

This dye composition applied for 25 minutes at ambient temperature to bleached hair gives the hair, after rinsing and shampooing, a salmon pink coloring.

EXAMPLE IX

The following dye composition is prepared:

| | |
|---|---|
| Dye of Example 5 | 3 g |
| $R(-OCH_2CH-CH_2OH)_2 \quad OH \quad R = oleyl$ | 3.7 g |
| $\quad R = oleyl$ | 5.5 g |
| $R(-OCH_2CH-CH_2OH)_4 \quad OH$ | |
| Propyleneglycol | 7.4 g |
| Ammonia at 22° Be q.s.p. | pH = 3 |
| Water q.s.p. | 100 g |

This dye composition is applied for 15 minutes at 20° C. to bleached hair. After rinsing and shampooing, the hair has a golden apricot coloring.

EXAMPLE X

The following dye composition is prepared:

| | |
|---|---|
| Dye of example 7 | 0.5 g |
| 96° ethyl alcohol | 25 g |
| Water q.s.p. | 100 g |
| Ammonia at 22° Be q.s.p. | pH = 10 |

This dye composition is applied to bleached hair for 20 minutes at ambient temperature. After rinsing and shampooing, the hair has a sulfur-yellow coloring.

EXAMPLE XI

The following dye composition is prepared:

| | |
|---|---|
| Dye of example 12 | 1 g |
| Butylglycol | 5 g |
| Lauric alcohol oxyethylened with 10.5 moles of ethylene oxide | 5 g |
| Ammonia at 22° Be q.s.p. | pH = 10 |

This dye composition, applied for 20 minutes at 20° C. to bleached hair, gives it a jonquil coloring.

EXAMPLE XII

The following dye composition is prepared:

| | |
|---|---|
| Dye of example 9 | 1 g |
| Ammonium laurylsulfate | 10 g |
| Water q.s.p. | 100 g |
| 2% phosphoric acid solution q.s.p. | pH = 6 |

This dye composition, applied for 25 minutes at 20° C. to 95% naturally white hair, gives it, after rinsing and shampooing, a very luminous greenish yellow coloring.

EXAMPLE XIII

The following dye composition is prepared:

| | |
|---|---|
| Dye of example 9 | 0.1 g |
| 96° ethyl alcohol | 25 g |
| Water q.s.p. | 100 g |
| Ammonia at 22° Be q.s.p. | pH = 10 |

This dye composition is applied to 95% naturally white hair for 20 minutes at ambient temperature. After rinsing and shampooing, it gives it a light greenish yellow coloring.

EXAMPLE XIV

The following dye composition is prepared:

| | |
|---|---|
| Dye of example 10 | 1.0 g |
| Butylglycol | 5 g |
| Lauric alcohol oxyethylened with 10.5 moles of ethylene oxide | 5 g |
| Triethanolamine q.s.p. | pH = 10 |
| Water q.s.p. | 100 g |

This dye composition, applied for 25 minutes at 35° C. to bleached hair, gives it, after rinsing and shampooing, a lemon yellow coloring.

EXAMPLE XV

The following dye composition is prepared:

| | |
|---|---|
| Dye of example 11 | 5 g |
| 96° ethyl alcohol | 25 g |
| Ammonia at 22° Be q.s.p. | pH = 10.5 |
| Water q.s.p. | 100 g |

This dye composition, applied for 10 minutes at 25° C. to bleached hair, gives it, after rinsing and shampooing, a very luminous jonquil coloring.

EXAMPLE XVI

The following dye composition is prepared:

| | |
|---|---|
| Dye of example 23 | 0.25 g |
| Vinyl acetate-crotonic acid copolymer (vinyl acetate, 90%, crotonic acid, 10%. Molecular weight 45,000 to 50,000) | 2 g |
| 96° ethanol | 50 g |
| Water q.s.p. | 100 g |
| 5% lactic acid solution q.s.p. | pH = 5 |

This dye composition, applied as a setting lotion to bleached hair, gives it a bright yellow shade.

EXAMPLE XVII

The following dye composition is prepared:

| | |
|---|---|
| Dye of example 24 | 0.65 g |
| Sodium laurylsulfate with 19% oxyethylened alcohol at the start | 20 g |
| Trilon B (ethylenediaminetetraacetic acid) | 0.2 g |
| Water q.s.p. | 100 g |
| Ammonia at 22° Be q.s.p. | pH = 9.8 |

This dye composition, applied to bleached hair for 20 minutes at ambient temperature, gives it, after rinsing and shampooing, a bright yellow coloring.

EXAMPLE XVIII

The following dye composition is prepared:

| | |
|---|---|
| Dye of example 13 | 0.4 g |
| Nonylphenol with 4 moles of ethylene oxide | 20 g |
| Nonylphenol with 9 moles of ethylene oxide | 20 g |
| Water q.s.p. | 100 g |
| Ammonia at 22° Be q.s.p. | pH = 10 |

This dye composition is applied for 20 minutes at ambient temperature to bleached hair. After rinsing and shampooing, it gives them a light greenish yellow coloring.

EXAMPLE XIX

The following dye composition is prepared:

| | |
|---|---|
| Dye of example 25 | 0.1 g |
| Vinyl acetate-crotonic acid copolymer (vinyl acetate 90%, crotonic acid 10%, molecular weight 45,000 to 50,000) | 1 g |
| 96° ethyl alcohol | 36 g |
| Water q.s.p. | 100 g |
| Triethanolamine q.s.p. | pH = 5.5 |

This dye composition, applied as a setting lotion to bleached hair, gives it a light golden blond shade.

EXAMPLE XX

The following dye composition is prepared:

| | |
|---|---|
| Dye of example 14 | 1 g |
| Carboxymethylcellulose | 5 g |
| Water q.s.p. | 100 g |
| 5% lactic acid solution q.s.p. | pH = 5 |

This dye composition is applied for 20 minutes at 35° C. to bleached hair. After rinsing and shampooing, it gives it an extremely luminous bright yellow coloring.

EXAMPLE XXI

The following dye composition is prepared:

| | |
|---|---|
| Dye of example 16 | 0.75 g |
| Diethylene glycol monomethyl ester | 10 g |
| Water q.s.p. | 100 g |
| 5% lactic acid solution q.s.p. | pH = 4 |

This dye composition is applied for 15 minutes at ambient temperature to bleached hair. After rinsing and shampooing, the hair has a strong orange coloring.

EXAMPLE XXII

The following dye composition is prepared:

| | |
|---|---|
| Dye of example 15 | 3 g |
| Carbopol 934 (acrylic acid polymer, molecular weight 2-3 million made by Goodrich Chemical Co.) | 4.5 g |
| Water q.s.p. | 100 g |
| Ammonia at 22° Be q.s.p. | pH = 8.5 |

This dye composition is applied for 20 minutes at 20° C. to bleached hair. After rinsing and shampooing, the hair is of a sulfur yellow coloring.

EXAMPLE XXIII

The following dye composition is prepared:

| | |
|---|---|
| Dye of example 17 | 0.5 g |
| Lauric alcohol with 10.5 moles of ethylene oxide | 20 g |
| Water q.s.p. | 100 g |
| Triethanolamine q.s.p. | pH = 7 |

This dye composition, applied for 20 minutes at ambient temperature to bleached hair, after rinsing and shampooing, gives the hair a golden coloring.

EXAMPLE XXIV

The following dye composition is prepared:

| | |
|---|---|
| Dye of example 19 | 0.5 g |
| 96° ethyl alcohol | 20 g |
| Carbopol 934 (acrylic acid polymer, molecular weight 2-3 million made by Goodrich Chemical Co.) | 3.7 g |
| Water q.s.p. | 100 g |
| 5% lactic acid solution q.s.p. | pH = 4 |

This dye composition, applied for 20 minutes at 20° C. to bleached hair, gives it, after rinsing and shampooing, a canary yellow coloring.

EXAMPLE XXV

The following dye composition is prepared:

| | |
|---|---|
| Dye of example 21 | 0.5 g |
| 60% polyvinylpyrrolidone 40% vinyl acetate copolymer (sold under the code PVP/VA 5630 by General Aniline and Film Corp.) | 2 g |
| Isopropanol | 35 g |
| Water q.s.p. | 100 g |
| Triethanolamine q.s.p. | pH = 7.5 |

This dye composition, applied as a setting lotion to bleached hair, gives it a brilliant yellow coloring.

EXAMPLE XXVI

The following dye composition is prepared:

| | |
|---|---|
| Dye of example 18 | 0.05 g |
| Polyvinyl pyrrolidone copolymer (sold under the code K30, average molecular weight of 40,000 by General Aniline and Film Corp.) | 2 g |
| Isopropanol | 25 g |
| Water q.s.p. | 100 g |
| Ammonia at 22° Be q.s.p. | pH = 7.5 |

This dye composition, applied as a setting lotion to bleached hair, gives it a pink champagne coloring.

EXAMPLE XXVII

The following dye composition is prepared:

| | |
|---|---|
| Dye of example 20 | 0.3 g |
| Polyvinylpyrrolidone 30%/vinyl acetate 70% | 2 g |
| 96° ethyl alcohol | 40 g |
| Water q.s.p. | 100 g |
| Ammonia at 22° Be q.s.p. | pH = 8 |

This dye composition, applied as a setting lotion to bleached hair, gives it a sulfur yellow coloring.

EXAMPLE XXVIII

The following dye composition is prepared:

| Dye of example 22 | 0.25 g |
|---|---|
| Ammonium laurylsulfate | 10 g |
| Water q.s.p. | 100 g |
| Ammonia at 22° Be q.s.p. | pH = 10 |

This dye composition, applied for 15 minutes at ambient temperature to bleached hair, after rinsing and shampooing, gives it a sulfur yellow coloring.

EXAMPLE XXIX

The following dye composition is prepared

| Dye of example 26 | 0,3 g |
|---|---|
| Nonylphenol with 4 moles of ethylene oxide | 8 g |
| Nonylphenol with 9 moles of ethylene oxide | 8 g |
| Ethylene glycol | 2 g |
| Water q.s.p. | 100 g |
| Ammonia at 22° Be q.s.p. | pH = 9,5 |

This dye composition, applied for 20 minutes at ambient temperature to bleached hair, after rinsing and shampooing, gives it a lemon yellow color.

The compounds of formula (I) are very important shading dyes since natural tints on hair are obtained by mixtures of dyes going from yellow to blue and it is then essential to be able to have dyes for hair giving real yellow or greenish yellow shades.

EXAMPLE A

The following dye composition is prepared:

| Dye of example 8 | 0.4 g |
|---|---|
| 1-N—β-hydroxyethylamino 2-nitro 4-(N'N'methyl, β-hydroxyethylamino)-benzene | 2 g |
| Diethanolamides of the fatty acids of coconut oils | 10 g |
| Water q.s.p. | 100 g |
| 5% lactic acid solution q.s.p. | pH = 7 |

This dye composition is applied to 95% naturally white hair for 20 minutes at ambient temperature. After rinsing and shampooing, the hair has an ash beige color.

EXAMPLE B

The following dye composition is prepared:

| Dye of example 7 | 1 g |
|---|---|
| Dye of example 9 | 1 g |
| Paraminophenol | 0.5 g |
| Paratoluylene diamine dihydrochloride | 0.5 g |
| Resorcinol | 1 g |
| 2,4-diamino anisol dihydrochloride | 0.5 g |
| Sodium laurylsulfate with 19% of starting oxyethylened alcohol | 20 g |
| Trilon B (ethylenediaminetetraacetic acid) | 0.2 g |
| Ammonia at 22° Be | 10 g |
| Water q.s.p. | 100 g |

To this dye composition is added an equal volume of 20 volume hydrogen peroxide. The final pH is 10.5. This mixture is applied for 20 minutes at ambient temperature to 95% naturally white hair. After rinsing and shampooing, the hair is of a brown shade with reddish-brown highlights.

EXAMPLE C

The operation is as in example A with the following dye composition:

| Dye of example 4 in hydrochloride form | 2 g |
|---|---|
| 1-amino 2-nitro 4-methylamino benzene | 0.5 g |
| Carboxymethylcellulose | 5 g |
| Water q.s.p. | 100 g |
| Ammonia at 22° Be q.s.p. | pH = 10 |

After rinsing and shampooing, the dye composition produces a very reddish copper shade.

EXAMPLE D

The following dye composition is prepared:

| Dye of example 1 | 0.25 g |
|---|---|
| Dye of example 8 | 0.5 g |
| Tetraaminoanthraquinone | 0.5 g |
| 1,4-diaminoanthraquinone | 0.5 g |
| Black diazo Cibacete | 0.25 g |
| 1-N—methylamino 2-nitro 4-(N'N'methyl, β-hydroxyethylamino)-benzene | 1 g |
| Nitroparaphenylenediamine | 0.025 g |
| Carboxymethylcellulose | 5 g |
| Ammonia at 22° Be q.s.p. | pH = 10 |
| Water q.s.p. | 100 g |

This dye composition, applied for 20 minutes at ambient temperature to bleached hair, gives the hair after rinsing and shampooing, a golden brown coloring.

EXAMPLE E

The operation is as in example D with the following dye composition:

| Dye of example 1 | 0.25 g |
|---|---|
| Dye of example 8 | 1 g |
| 1-N—methylamino 2-nitro 4-(N',N'methyl, β-hydroxyethylamino)benezene | 2 g |
| Black diazo cibacete | 0.5 g |
| 1-N—methylamino 4-γ-aminopropylamino anthraquinone | 0.75 g |
| 1,4-diamino anthraquinone | 0.4 g |
| Carboxymethylcellulose | 5 g |
| Ammonia at 22° Be q.s.p. | pH = 9 |
| Water q.s.p. | 100 g |

A bronze green color is obtained.

EXAMPLE F

The following dye composition is prepared:

| Dye of example 8 | 0.1 g |
|---|---|
| N—[4-(di-β-hydroxyethylamino) phenyl]2,6-dimethyl 3-amino benzoquinone imine | 0.05 g |
| 1,4-di[β(β hydroxyethoxy) ethyl] amino anthraquinone | 0.05 g |
| Crotonic acid-vinyl acetate copolymer (90% vinyl acetate, 10% crotonic acid, molecular weight 45,000 to 50,000) | 2 g |
| 96° ethyl alcohol | 50 g |
| Water q.s.p. | 100 g |
| Triethanolamine q.s.p. | pH = 7 |

This mixture, applied as a setting lotion to bleached hair, gives the hair an ash gray coloring with mauve glints.

EXAMPLE G

The operation is as in example D with the following dye composition:

| | |
|---|---|
| Dye of example 8 | 0.5 g |
| Dye of example 7 | 0.5 g |
| Black diazo cibacete | 1 g |
| Nitroparaphenylene diamine | 0.2 g |
| 1,4-diamino anthraquinone | 0.2 g |
| Tetraamino anthraquinone | 0.2 g |
| Diethanolamides of copra fatty acids | 10 |
| Water q.s.p. | 100 g |
| Ammonia at 22° Be q.s.p. | pH = 9.5 |

A copper coloring is obtained.

EXAMPLE H

The operation is as in example F with the following dye composition:

| | |
|---|---|
| Dye of example 5 in hydrochloride form | 1 g |
| Dye of example 9 | 0.2 g |
| N—[(4'-amino)phenyl] 2-methyl 5-amino benzoquinone imine | 0.2 g |
| Vinyl acetate-crotonic acid copolymer (90% vinyl acetate, 10% crotonic acid, molecular weight 45,000 to 50,000) | 2 g |
| 96° ethyl alcohol | 50 g |
| Water q.s.p. | 100 g |
| Triethanolamine q.s.p. | pH = 7 |

A hazel coloring is obtained.

EXAMPLE I

The operation is as in example D with the following dye composition:

| | |
|---|---|
| Dye of example 8 | 1 g |
| 2-N—$\beta$-hydroxyethylamino (2-methoxy 3,5-dimethyl 4-amino) 5-anilino 1,4-benzoquinone | 1 g |
| Tetraamino anthraquinone | 0.5 g |
| 1,4-diamino anthraquinone | 0.25 g |
| 1-N—methylamino 2-nitro 4-(N'—N'methyl, $\beta$ hydroxyethyl) amino benzene | 1.5 g |
| Black diazo cibacete | 0.6 g |
| Nitroparaphenylene diamine | 0.2 g |
| Diethanolamides of coconut oil fatty acids (copra fatty acids) | 10 g |
| Ammonia at 22° Be q.s.p. | pH = 10 |

A fawn coloring is obtained.

EXAMPLE J

The following dye composition is prepared:

| | |
|---|---|
| Dye of example 6 in hydrochloride form | 0.9 g |
| 1-N—methylamino 2-nitro 4-(N'N'—methyl, $\beta$-hydroxyethylamino) benzene | 0.125 g |
| Carboxymethylcellulose | 5 g |
| Ammonia at 22° Be q.s.p. | pH = 8.5 |
| Water q.s.p. | 100 g |

This dye composition, applied for 25 minutes at 25° C. to 95% naturally white hair, gives it an ash beige coloring.

EXAMPLE K

The following dye composition is prepared:

| | |
|---|---|
| Dye of example 18 | 0.5 g |
| Dye of example 2 | 0.5 g |
| Dye of example 21 | 0.25 g |
| Dye of example 12 | 0.25 g |
| 1,4-diamino anthraquinone | 0.5 g |
| Tetraaminoanthraquinone | 0.25 g |
| Sodium laurylsulfate with 19% starting oxyethylened alcohol | 20 g |
| Trilon B (ethylenediaminetetraacetic acid) | 0.2 g |
| Water q.s.p. | 100 g |
| Ammonia at 22° Be q.s.p. | pH = 10 |

This dye composition is applied for 15 minutes at ambient temperature to 95% naturally white hair. After rinsing and shampooing, it gives it a copper coloring.

EXAMPLE L

By operating as in the previous example, a tin gray coloring is obtained with the following dye composition:

| | |
|---|---|
| Dye of example 9 | 0.1 g |
| 1-hydroxy 4-$\beta$-hydroxyethylamino anthraquinone | 0.5 g |
| Carbopol 934 acrylic acid polymer molecular weight 2-3 million | 4.76 g |
| 96° ethanol | 20 g |
| Water q.s.p. | 100 g |
| Ammonia at 22° Be q.s.p. | pH = 10 |

EXAMPLE M

The following dye composition is prepared

| | |
|---|---|
| Dye of example 28 | 0,5 g |
| Ammonium alkyl sulfate | 15 g |
| Lauric alcohol reacted with 10.5 moles of ethylene oxide | 5 g |
| Water q.s.p. | 100 g |
| Ammonia at 22° Be q.s.p. | pH = 10 |

This dye composition, applied for 20 minutes at ambient temperature to bleached hair, after rinsing and shampooing, gives it a pale yellow color.

The present invention also relates to dyeing compositions for human hair that contain in solution at least an ether oxide of the general formula:

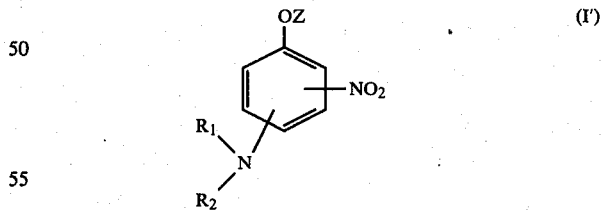

(I')

wherein Z represents a substituted lower alkyl radical, $R_1$ and $R_2$, identical or different, can be a hydrogen atom, a lower alkyl radical or a substituted lower alkyl radical identical with or different from Z and functional groups $NO_2$ and $NR_1R_2$ can occupy on the ring all positions in relation to OZ.

It has now been found that the compounds of formula (I') in which the radical Z is a substituted lower alkyl radical chosen from the carbalkoxyaminoalkyl, alkoxyalkyl, N,N-dialkylcarbamylalkyl, acylaminoalkyl, ureidoaminoalkyl, mesylaminoalkyl and

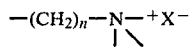

group also have a good affinity for hair and give a good equalizing color to partially sensitized hair.

The present invention therefore also relates to dyeing compositions for human hair that contain in solution at least an ether oxide of the general formula:

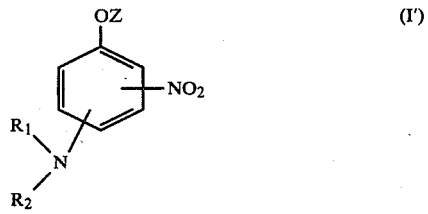

wherein Z represents a substituted lower alkyl radical selected from the carbalkoxyaminoalkyl, alkoxyalkyl, N,N-dialkylcarbamylalkyl, acylaminoalkyl, ureidoalkyl, mesylaminoalkyl and

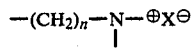

group, n being a whole number from 1 to 6 and $X^\ominus$ is an anionic residue, in particular a halogen or a $CH_3SO_4$ radical. The compositions according to the invention are aqueous or water-alcohol solutions which are easily prepared by dissolving in water or in a water-alcohol mixture, one or more of the compounds of formula (I'). The alcohols used in these compositions are generally in a proportion of 20 to 75% by weight and preferably from 25 to 50%. These alcohols are preferably ethanol or isopropanol.

The concentration of the compounds of formula (I') in the dyeing compositions according to the invention can vary in broad ranges because of their good affinity for hair. This concentration is generally between 0.001 and 5% by weight, and, preferably between 0.05 and 5% by weight.

The pH of the compositions according to the invention is generally between 3 and 11.5 and, preferably, between 3 and 10.5. It is adjusted to the desired value by addition of an acid such as phosphoric acid or lactic acid or a base such as triethanolamine or ammonia.

The compositions according to the invention can contain various adjuvants usually used in cosmetics, for example, wetting agents, dispersing agents, swelling agents, penetration agents, emollients or perfumes. They can also contain solvents such as glycols and glycol esters.

The compositions according to the invention can also contain other direct dyes such as azo or anthraquinone dyes, nitro dyes of the benzene series, indoanilines, indophenols or indamines.

The compositions according to the invention can be used for the purposes of lasting dyeing of the hair: in this case, they are applied to the hair for a period varying from 3 to 30 minutes, this application being followed by a rinsing and possibly a washing and drying of the hair.

The compositions according to the invention can also be used in the form of hair setting lotions, intended both to give the hair a slight coloring and improve the holding of the setting: in this case they can be in the form of water-alcohol solutions containing at least a cosmetic resin and their application is performed on wet hair previously washed and rinsed and which is then rolled up and dried.

The cosmetic resins going into the composition of these lotions for hair setting are used in a proportion of 1 to 3% by weight and preferably 1 to 2% by weight and in particular can be polyvinylpyrrolidone, the copolymers of crotonic acid-vinyl acetate, vinylpyrrolidone-vinyl acetate and maleic anhydride-butylvinyl ether, maleic anhydride/methyl vinyl ether and its ethyl, isopropyl and butyl esters.

The setting lotions according to the invention generally contain 20–75% by weight and preferably 25 to 50% by weight of low molecular weight alcohol which is preferably ethanol or isopropanol.

The compositions according to the invention can also be used in the form of oxidation dyes. Such dyeing mixtures contain oxidation bases such as paratoluenediamine and para-aminophenol and/or couplers such as meta-aminophenol, meta-diamino-anisole and resorcinol.

In the processes using oxidation dyes, the dyeing composition is prepared at the time of application to the hair by addition of an oxidizing agent such as hydrogen peroxide to an ammonia solution of one or more oxidation "bases" and/or "couplers". The hydrogen peroxide is used in a concentration of 2.4% (8 volumes) to 9% (30 volumes). However, in the case of "self-oxidizing" compounds the application of the composition can take place with or without addition of hydrogen peroxide. It is also possible to use peroxides or persalts are the oxidizing agent.

As paraphenylenediamines acting as usable oxidation bases in the compositions according to the invention, there can be cited primary, secondary and tertiary paraphenylenediamines, possibly substituted on the benzene ring and preferably those represented by the general formula

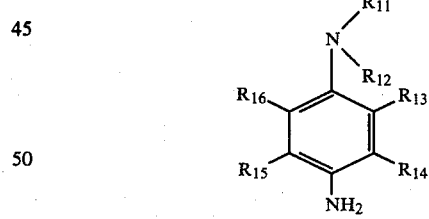

wherein $R_{11}$ and $R_{12}$, identical or different, can signify hydrogen, a lower straight chain or branched alkyl group, mono- or polyhydroxyl alkyl, piperidinoalkyl, carbamylalkyl, dialkyl carbamylalkyl, aminoalkyl, monoalkylaminoalkyl, dialkylaminoalkyl, $\omega$-aminosulfonylalkyl, carboxyalkyl, alkylsulfonamidoalkyl, arylsulfonamidoalkyl, morpholinoalkyl, acylaminoalkyl, sulfoalkyl, groups in which the alkyl radical comprises preferably 1 to 4 carbon atoms, $R_{11}$ and $R_{12}$ also being able to form together a heterocyclic group with five or six groupings, such as morpholine or piperidine.

$R_{13}$, $R_{14}$, $R_{15}$ and $R_{16}$ signify independently of one another, a hydrogen or halogen atom, a lower alkyl or lower alkoxy group, comprising preferably 1 to 4 carbon atoms.

In said compounds halogen can signify fluorine, bromine but preferably chlorine.

By way of particularly effective compounds in the compositions according to the invention, there can be cited paraphenylene diamine, paratoluylene diamine, methoxy paraphenylene diamine, chloroparaphenylene diamine, 2,6-dimethyl paraphenylene diamine, 2,5-dimethyl paraphenylene diamine, 2-methyl 5-methoxy paraphenylene diamine, 2,6-dimethyl 5-methoxy paraphenylene diamine, N,N-dimethyl paraphenylene diamine, 3-methyl 4-amino N,N-(diethyl) aniline, N,N-(di β-hydroxy ethyl) paraphenylene diamine, 3-methyl 4-amino N,N-(di β-hydroxyethyl)aniline, 3-chloro-4-amino N,N-(di β-hydroxethyl) aniline, 4-amino N,N-(ethyl, carbamylmethyl) aniline, 3-methyl 4-amino N,N-(ethyl, carbamylmethyl) aniline, 4-amino N,N-(ethyl, moropholinoethyl) aniline, 3-methyl 4-amino N,N-(ethyl, morpholinoethyl) aniline, 4-amino N,N-(ethyl, acetylaminoethyl) aniline, 3-methyl 4-amino N,N-(ethyl, acetylaminoethyl) aniline, 4-amino N,N-(ethyl, mesylaminoethyl) aniline, 3-methyl 4-amino N,N-(ethyl, mesylaminoethyl) aniline, 4-amino N,N-(ethyl, β-sulfoethyl) aniline, 3-methyl 4-amino N,N-(ethyl, β-sulfoethyl) aniline, N-[(4'-amino) phenyl] morpholine, N-[(4'-amino) phenyl] piperidine, 4-amino, N,N-(ethyl, piperidinoethyl) aniline, 3-methyl 4-amino N-methyl aniline, 2-chloro 4-amino N,N-(ethyl, sulfonamidomethyl) aniline, 2-chloro 4-amino N-(ethyl) aniline and 2-methyl 4-amino N-(β-hydroxyethyl) aniline.

These paraphenylene diamines can be introduced into the dyeing composition in the form of free base or in salified form, for example in the form of mono, di- or tri-hydrochloride or hydrobromide or sulfate.

Among the other oxidation "bases" there can be cited: para-aminophenol, 2-methyl 4-amino phenol, 3-methyl 4-amino phenol, 2-chloro 4-amino phenol, 3-chloro 4-amino phenol, 2,6-dimethyl 4-amino phenol, 3,5-dimethyl 4-amino phenol, 2,3-dimethyl 4-amino phenol, 2,5-dimethyl 4-amino phenol, 2,5-diamino pyridine, 2-dimethylamino 5-amino pyridine, 2-diethylamino 5-amino pyridine, 3-methyl 7-amino phenomorpholine and 5-amino indole.

The dyeing compositions, object of the present application, can further contain one or more ether oxides and one or more oxidation bases or couplers. The usable couplers in the compositions according to the invention have the general formula:

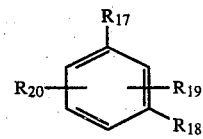

wherein $R_{17}$ and $R_{18}$, identical or different, can signify hydroxy, —NHR where R can be a hydrogen atom, an acyl, ureido, carbalkoxy, carbamylalkyl, alkyl, dialkylcarbamylalkyl or hydroxyalkyl group; $R_{17}$ and $R_{18}$ can also signify hydrogen, alkoxy and alkyl provided at least one of the substituents $R_{17}$ and $R_{18}$ designate OH. $R_{19}$ and $R_{20}$ can designate hydrogen, alkyl branched or not, alkoxy, halogen, amino possibly substituted by an alkyl, acylamino or ureido group.

Of the couplers having to the above general formula, there will be cited more particularly resorcinol, meta-aminophenol, 2,4-diamino anisole, 2-methyl-5-ureido phenol, 2,6-dimethyl aminophenol, 2-methyl 5-acetylamino phenol, 2,6-dimethyl 5-acetylamino phenol and 3-amino 4-methoxy phenol.

Other couplers usable in the compositions according to the invention are, for example, heterocyclic compounds such as in particular 6-hydroxy phenomorpholine, 6-amino phenomorpholine, derivatives of pyridine, pyrazolones and diketonic compounds, or again α-naphthol or hydroquinones.

The diketonic compounds more particularly usable in the compositions according to the invention have to the formula

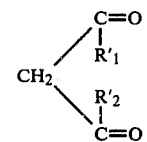

wherein $R'_1$ and $R'_2$ signify independently of one another alkyl, preferably lower alkyl having 1 to 4 carbon atoms, alkoxy, phenyl,

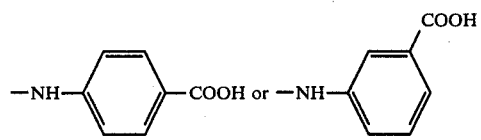

Of the pyrazolones used in the compositions according to the invention, there are preferably used those having to the formula

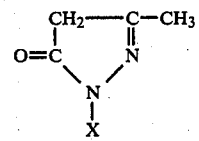

wherein X signifies phenyl substituted or not, by —SO₃H and/or halogen. By the term halogen is understood fluorine, bromine and preferably chlorine.

The oxidation base concentration is between 0.001 and 5% and preferably between 0.03 and 2% and that of the coupler is between 0.001 and 5% by weight, and preferably between 0.015 and 2%.

The present invention also has for its object compounds of the general formula

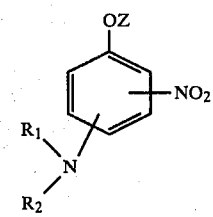

(I')

wherein Z represents a substituted lower alkyl radical selected from carbalkoxyaminoalkyl, alkoxyalkyl, N,N-diakylcarbamylalkyl, acylaminoalkyl, ureidoalkyl, mesylaminoalkyl and

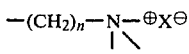

where $X^{\ominus}$ is an anionic residue, in particular a halogen atom or $CH_3SO_4$ and $R_1$ and $R_2$, identical or different, can be a hydrogen atom, a lower alkyl radical or a substituted lower alkyl radical, identical or different from Z, and the functional groups $NO_2$ and $NR_1R_2$ can occupy all positions on the ring in relation to OZ.

The compounds of formula (I') are obtained the action, in DMF, of alkylizing agents of the formula XZ, wherein X represents a halogen atom and Z a substituted alkyl radical, on alkaline salts of formula (II) in a molar ratio of alkylation agent to said alkaline salt between 1 and 11 and preferably 1.1 and 4.

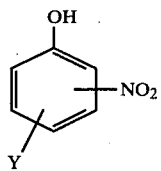 (II')

wherein Y can represent $NH_2$, $NHR_1$ groups,

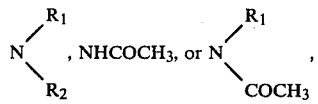

$R_1$ and $R_2$ have the values mentioned above, or again a halogen atom such as Cl, Br or F; $NO_2$ and Y can occupy all the positions on the ring in relation to OH, except in the case where Y is a halogen atom, in which case this halogen atom will be in the ortho or para position of the $NO_2$ group, with the formation of the compound of formula (III')

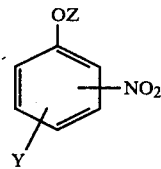 (III')

and by possible treatment of compound (III') to transform the Y group into the final $NR_1R_2$ group.

The reaction can also be performed in HMPT (hexamethylphosphorotriamide). The reaction temperatures are in the range of 50° to 120° C. and preferably between 70° and 100° C.

In case Y represents a halogen atom, an amine is made to react on the compound (III') obtained.

As types of amines used in this reaction, there can be considered, for example, methylamine, butylamine, ethanolamine and β-diethylaminoethylamine.

In case Y represents

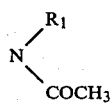

compound (III') is treated with hydrochloric acid, which leads to a compound (I') in which $R_2$ has the hydrogen value.

Then new substitutions can be made on the amine function of compound (I') by performing, for example, a new condensation of said compound with compound XZ.

Of the XZ compounds there can be cited, among others, glycol bromohydrin, diethylamino ethylchloride and chloracetamide.

The alkaline salts of compounds (II') can be prepared in a first stage by treating said compounds (II') with an aqueous or water-alcohol solution of potassium or sodium hydroxide. However, they can be obtained directly by adding potassium or sodium hydroxide in dimethylformamide, i.e., in the reaction medium in which XZ condensation is performed.

There will be indicated below some examples of preparation by way of illustrative and non-limiting example.

EXAMPLE 29

Preparation of (3-nitro 4-amino) phenyl, N,N-diethylcarbamylmethyl ether

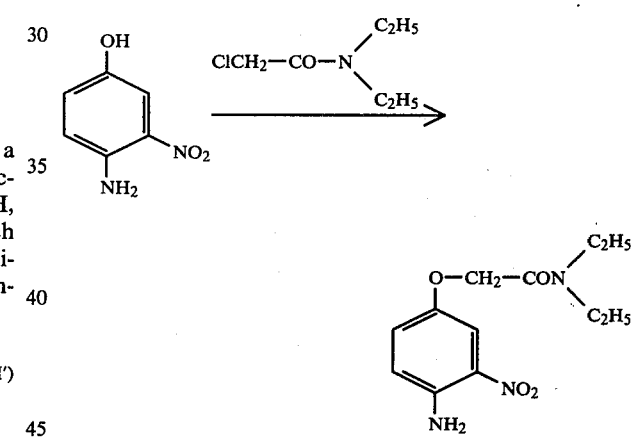

There is dissolved 0.04 mole (6.16 g) of 3-nitro 4-amino phenol in 20 cc of hexamethylphosphorotriamide (HMPT) and 5 cc of acetone. To this solution is added 0.06 mole (8.28 g) of potassium carbonate. This mixture, previously brought to 70° C., has added to it, gradually and with agitation, 0.062 mole (9.34 g) of N,N-diethyl chloroacetamide. The reaction temperature is kept at 75° C. for three hours. After cooling, the reaction mixture is poured into 80 ml of ice water. The expected product, which has precipitated, is drained and washed with water. After recrystallization in a 5% water-alcohol solution and drying under vacuum, the product melts at 145° C.

| ANALYSIS | CALCULATED FOR $C_{12}H_{17}N_3O_4$ | FOUND |
| --- | --- | --- |
| C % | 53.93 | 53.80 |
| H % | 6.37 | 6.36 |
| N % | 15.73 | 15.77 |

EXAMPLE 30

Preparation of [3-(N-methylamino)4-nitro]phenyl N,N-diethylcarbamylmethyl ether]

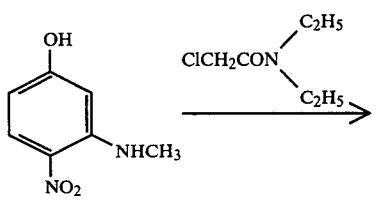

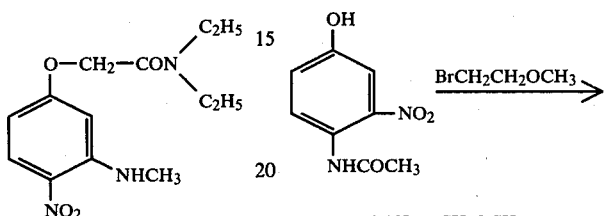

There are dissolved 0.04 mole (6.74 g) of 3-(N-methyl amino) 4-nitro phenol in 20 cc of hexamethylphosphorotriamide and 5 cc of acetone. To this solution is added 0.06 mole (8.28 g) of potassium carbonate. To this mixture, previously brought to 70° C., is added 0.062 mole (9.34 g) of N,N-diethylchloroacetamide. The reaction temperature is kept at 75° C. for an hour and a half. This mixture is then poured into 80 cc of ice water. The expected product precipitates in the form of an oil that rapidly crystallizes. The product is drained, washed with water, and recrystallized with a 50% water-alcohol solution. After drying under vacuum, the product melts at 92° C.

| ANALYSIS | CALCULATED FOR $C_{13}H_{19}N_3O_4$ | FOUND |
|---|---|---|
| C % | 55.52 | 55.41 |
| H % | 6.76 | 6.71 |
| N % | 14.95 | 14.91 |

EXAMPLE 31

Preparation of (3-methylamino 4-nitro)phenyl, β-methoxyethylether

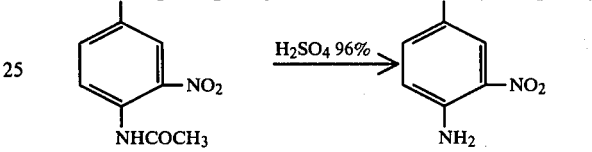

There is introduced 0.03 mole (5 g) of 3-(N-methylamino) 4-nitro phenol in 30 ml of hexamethylphosphorotriamide (HMPT). There is added 0.033 mole (4.6 g) of dry potassium carbonate. This mixture is heated in a double boiler at 80° C. then 0.033 mole (4 g) of 2-methoxy bromoethane is added. The reaction mixture is kept for 4 hours in the boiling double boiler then after cooling is poured into 150 ml of 0.5 N iced sodium solution. The expected product precipitates in crystallized form. It is drained, washed with water and recrystallized in acetone. It melts at 94° C.

| ANALYSIS | CALCULATED FOR $C_{10}H_{14}N_2O_4$ | FOUND |
|---|---|---|
| C % | 53.09 | 53.24 |
| H % | 6.24 | 6.28 |
| N % | 12.38 | 12.52 |

EXAMPLE 32

Preparation of (3-nitro 4-amino) phenyl-β-methoxyethyl ether

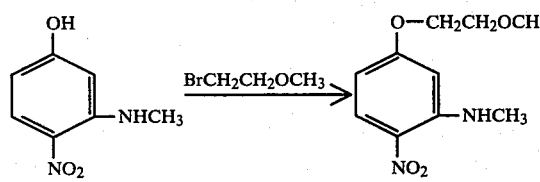

First stage

Preparation of (3-nitro 4-acetylamino) phenyl, β-methoxyethyl ether

There is introduced 0.7 mole (137.2 g) of 3-nitro 4-acetylamino phenol in 600 ml of hexamethylphosphorotriamide. There is added 0.77 mole (106.3 g) of anhydrous potassium carbonate. It is heated at 60° C., then there is added gradually with agitation 0.77 mole (107 g) of 2-methoxy bromoethane.

The reaction mixture is heated for 4 hours in a boiling double boiler then poured, after cooling, into 2.5 l of 0.5 N ice sodium solution.

The expected product precipitates. It is drained, washed with water and recrystallized in ethanol. After drying, it melts at 80° C.

Second stage

Preparation of (3-nitro 4-amino) phenyl β-methoxy ethyl ether

There is dissolved 0.0157 mole (4 g) of (3-nitro 4-acetylamino) phenyl β-methoxy ethyl ether in 10 ml of 96% sulfuric acid. The reaction mixture is kept at 80° C. for three hours, then poured into 30 ml of ice water. It is neutralized with ammonia at 22° Baume, then the expected product, which has precipitated in crystallized form, is drained. After recrystallization in isopropanol and drying under vacuum, the product melts at 89° C.

| ANALYSIS | CALCULATED FOR $C_9H_{12}N_2O_4$ | FOUND |
|---|---|---|
| C % | 50.94 | 50.81 |
| H % | 5.70 | 5.59 |
| N % | 13.20 | 13.34 |

EXAMPLE 33

Preparation of (3-nitro 4-methylamino) phenyl β-methoxy ethyl ether.

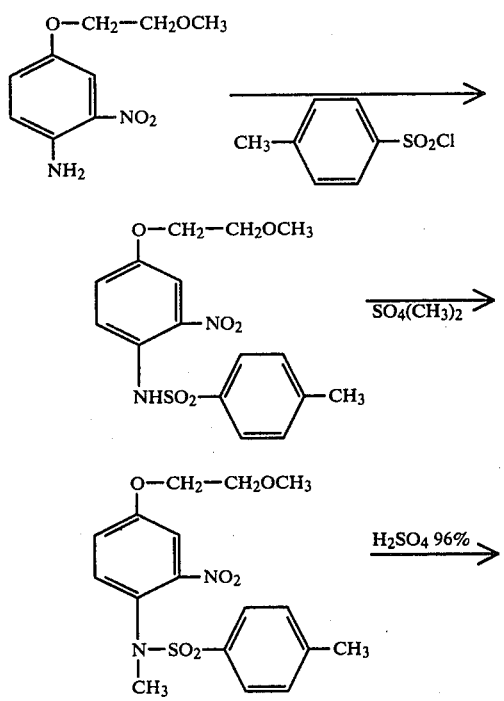

First stage

Preparation of (3-nitro 4-paratoluenesulfonylamino) phenyl β-methoxy ethyl ether There is dissolved 0.05 mole (10.61 g) of (3-nitro 4-amino)phenyl β-methoxy ethyl ether (described in example 32) in 20 ml of pyridine. There is added, gradually with agitation, 0.06 mole (11.4 g) of paratoluene sulfochloride. The temperature is raised to 50° C. The reaction medium is kept for four hours at this temperature then poured into 200 ml of 2 N iced hydrochloric solution. The expected product precipitates in the form of a very thick oil. This oil is dissolved in 100 ml of 2 N sodium solution, an insoluble light element is filtered and the sulfonamide is made to reprecipitate by acidification of the filtrate with acetic acid. The oily product, isolated by decantation, is used for the second stage.

Second stage

Preparation of [3-nitro 4-(N-methyl, N-paratoluene sulfonylamino)]phenyl β-methoxy ethyl ether The oil previously obtained is dissolved in 60 ml of 1 N sodium solution. There are added, gradually with agitation and at ambient temperature, 10.6 ml of methyl sulfate and simultaneously the amount of 4 N sodium solution necessary to maintain the alkaline pH.

The reaction medium is left over night at ambient temperature. The expected product has precipitated in crystallized form. It is drained, washed with water and recrystallized in ethanol. After drying, it melts at 91° C.

Third stage

Preparation of (3-nitro 4-methylamino) phenyl, β-methoxy ethyl ether

There is slowly dissolved, at ambient temperature, 0.034 mole (13 g) of [3-nitro 4-(N-methyl, N-paratoluenesulfonyl amino)]phenyl, β-methoxy ethyl ether in 26 ml of 96% sulfuric acid. The reaction medium is kept at ambient temperature for four hours, then poured into 600 g of ice. The expected product, which has precipitated in crystallized form, is drained. After washing with water, drying and recrystallization in cyclohexane, it melts at 54° C.

| ANALYSIS | CALCULATED FOR $C_{10}H_{14}N_2O_4$ | FOUND |
|---|---|---|
| C % | 53.09 | 53.07 |
| H % | 6.24 | 6.32 |
| N % | 12.38 | 12.43 |

EXAMPLE 34

Preparation of (3-nitro 4-β-hydroxyethylamino) phenyl, β-methoxy ethyl ether

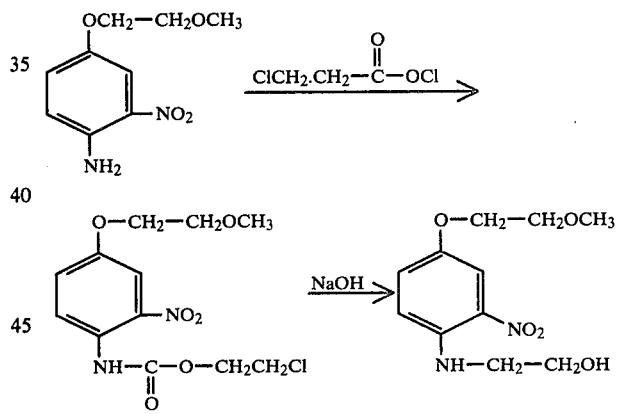

First stage

Preparation of [(2-nitro 4-β-methoxy ethyl ethoxy) phenyl]carbamate of β-chloroethyl There is introduced 0.05 mole (10.61 g) of (3-nitro 4-amino) phenyl β-methoxy ethyl ether (described in example 32) in 25 ml of dioxane. There is added 0.028 mole (2.8 g) of calcium carbonate. The reaction mixture is heated in a boiling double boiler, then there is added, gradually with agitation, 0.055 mole (7.9 g) of chloroethylchloroformate.

With the addition completed, the heating in the boiling double boiler is continued for two hours. The reaction mixture is poured on 100 ml of iced 0.5 N hydrochloric solution. The expected product precipitates in the form of an oil which is isolated by decantation and used directly in the second stage of the synthesis.

Second stage

Preparation of (3-nitro 4-β-hydroxyethylamino) phenyl, β-methoxy ethyl ether The oil isolated during the first stage of the synthesis is heated, with agitation, four hours with reflux, in 50 ml of a 4 N sodium solution.

After cooling, it is neutralized with a 5 N hydrochloric solution, then the expected product, which has precipitated in crystallized form, is drained. After washing with water, drying and recrystallization in benzene, the product melts at 66° C.

| ANALYSIS | CALCULATED FOR $C_{11}H_{16}N_2O_5$ | FOUND |
|---|---|---|
| C % | 51.56 | 51.37 |
| H % | 6.29 | 6.19 |
| N % | 10.93 | 11.06 |

EXAMPLE 35

Preparation of (3-nitro 6-amino) phenyl, β-methoxy ethyl ether

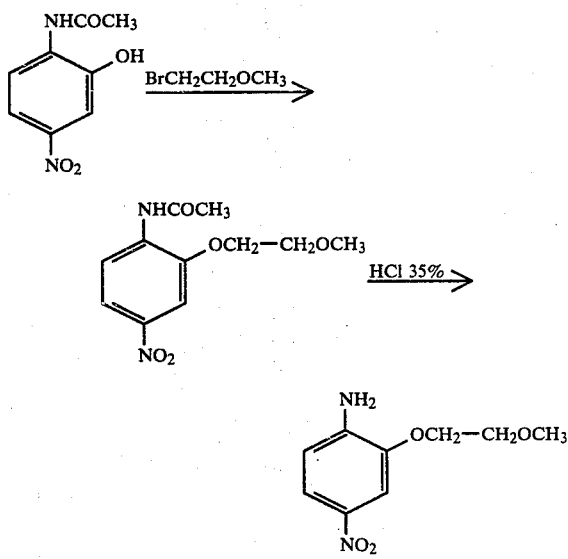

First stage

Preparation of (3-nitro 6-acetylamino) phenyl β-methoxy ethyl ether

There is introduced 0.04 mole (7.8 g) of 3-nitro 6-acetylamino phenol in 40 ml of hexamethylphosphorotriamide. There is added 0.044 mole (6.1 g) of dry potassium carbonate. The mixture is heated in the neighborhood of 60° C. then there is added 0.044 mole (6.1 g) of 2-methoxy bromoethane. The reaction mixture is kept in a boiling double boiler for two hours then poured into 200 ml of an iced 0.5 N sodium solution. The expected product precipitates. It is drained, washed with water and recrystallized in acetonitrile. After drying it melts at 130° C.

Second stage

Preparation of (3-nitro 6-amino) phenyl, β-methoxy ethyl ether

There is introduced 0.0157 mole (4 g) of (3-nitro 6-acetylamino) phenyl, β-methoxy ethyl ether in 12 ml of 35% hydrochloric acid. The reaction mixture is heated for an hour in a boiling double boiler. After cooling, 20 ml of water are added. The expected product, which has precipitated in crystallized form, is drained. After washing with water, recrystallization in isopropanol and drying under vacuum, the product melts at 125° C.

| ANALYSIS | CALCULATED FOR $C_9H_{12}N_2O_4$ | FOUND |
|---|---|---|
| C % | 50.94 | 50.86 |
| H % | 5.70 | 5.59 |
| N % | 13.20 | 13.36 |

EXAMPLE 36

Preparation of (4-nitro 2-amino) phenyl β-methoxy ethyl ether

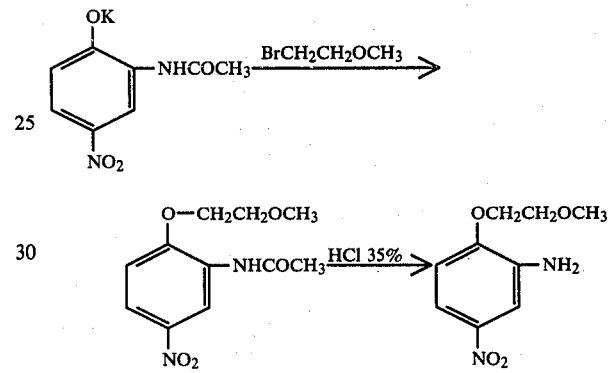

First stage

Preparation of (4-nitro 2-acetylamino) phenyl, β-methoxy ethyl ether

There is introduced 0.05 mole (11.7 g) of potassium salt of 4-nitro 2-acetylamino phenol in 40 ml of dimethylformamide (DMF). This mixture is brought to 90° C., then there is gradually added with agitation 0.054 mole (7.6 g) of 2-methoxy bromoethane. The temperature is kept at 90° C. for three hours. The cooled reaction mixture is poured into 200 ml of 1 N sodium solution. The expected product, which has precipitated, is drained and washed with water. It melts at 104° C.

Second stage

Preparation of (4-nitro 2-amino) phenyl, β-methoxy ethyl ether

There is introduced 0.01 mole (2.54 g) of (4-nitro 2-acetylamino) phenyl, β-methoxy ethyl ether in 5 ml of 35% hydrochloric acid. The hydrochloric solution is heated in a boiling double boiler for 30 minutes then 20 ml of ice water are added. After neutralization with ammonia, the expected product is precipitated in crystallized form. It is drained, washed with water and recrystallized in ethyl acetate. After drying under vacuum it melts at 97° C.

| ANALYSIS | CALCULATED FOR $C_9H_{12}N_2O_4$ | FOUND |
|---|---|---|
| C % | 50.94 | 50.74 |
| H % | 5.70 | 5.79 |

| ANALYSIS | CALCULATED FOR $C_9H_{12}N_2O_4$ | FOUND |
|---|---|---|
| N % | 13.20 | 13.39 |

EXAMPLE 37

Preparation of (3-nitro 6-amino) phenoxyethylamine hydrochloride

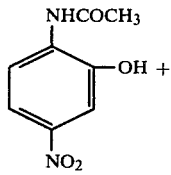

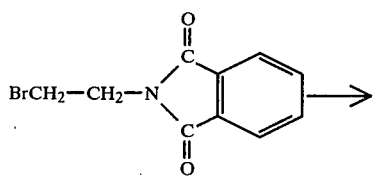

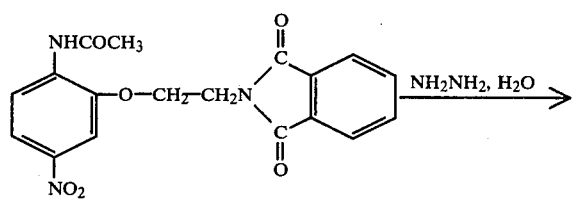

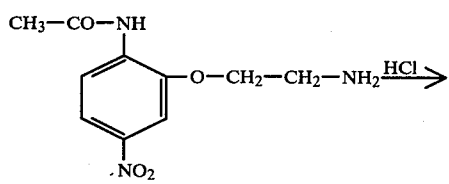

First stage

Preparation of (3-nitro 6-acetylamino) phenyl, β-phthalimido ethyl ether

There is dissolved 0.02 mole (3.9 g) of 3-nitro 6-acetylamino phenol in 20 ml of hexamethylphosphorotriamide. To this solution are added 0.022 mole (3.04 g) of potassium carbonate and 0.022 mole (5.6 g) of β-bromoethylphthalimide. The reaction mixture is heated in a boiling double boiler for three hours. After cooling, this mixture is poured into 100 cc of iced normal sodium solution. The expected product, which has precipitated, is drained. After washing with water, recrystallization in acetic acid and drying under vacuum at 50° C. the product melts at 265° C.

| ANALYSIS | CALCULATED FOR $C_{18}H_{15}N_3O_6$ | FOUND |
|---|---|---|
| C % | 58.53 | 58.38 |
| H % | 4.09 | 4.08 |
| N % | 11.38 | 11.54 |

Second stage

Preparation of (3-nitro 6-acetylamino) phenoxyethylamine

There are heated for two hours in a boiling double boiler 0.057 mole (21 g) of (3-nitro 6-acetylamino) phenyl β-phthalimido ethyl ether and 5.5 ml of 98% hydrazine hydrate in 250 ml of normal propyl alcohol. After cooling for the reaction mixture and addition of 150 ml of 0.5 N sodium solution, the initial product, which has not reacted, is recovered by draining. The filtrate is acidified with hydrochloric acid to eliminate, by draining, the insoluble phthalhydrazide formed in the acid medium. After neutralization of the new filtrate with ammonia, the expected product, after concentration under vacuum, is precipitated in the hydrochloride form.

This hydrochloride is treated with a normal sodium solution. The (3-nitro 6-acetylamino) phenoxyethylamine is drained and washed with water and, after recrystallization in isopropanol and drying under vacuum at 50° C., it melts at 132° C.

Third stage

Preparation of (3-nitro 6-amino) phenoxyethylamine hydrochloride

There is heated for 5 hours in a boiling double boiler 0.02 mole (4.78 g) of (3-nitro 6-acetylamino) phenoxyethylamine in 15 cc of 35% hydrochloric acid. After cooling, 5 cc of water are added and the solution is neutralized with ammonia. The expected hydrochloride is drained. After washing with a dilute hydrochloric solution, recrystallization with a water-alcohol solution and drying under vacuum, the product melts with decomposition around 260° C.

| ANALYSIS | CALCULATED FOR $C_8H_{12}N_3O_3Cl$ | FOUND |
|---|---|---|
| C % | 41.12 | 41.14 |
| H % | 5.18 | 5.14 |
| N % | 17.98 | 18.14 |
| Cl % | 15.17 | 15.27 |

EXAMPLE 38

Preparation of (3-nitro 6-amino) phenyl, mesylaminoethyl ether

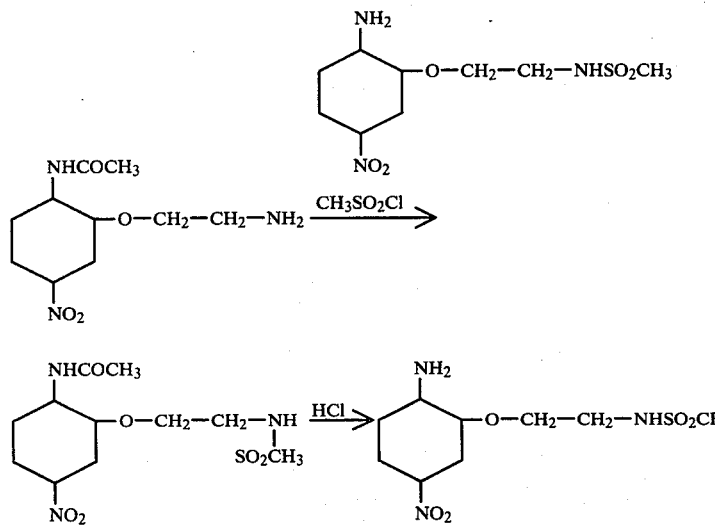

First stage

Preparation of (3-nitro 6-acetylamino) phenyl, mesylaminoethylether

There is introduced 0.01 mole (2.4 g) of (3-nitro 6-acetylamino) phenoxyethylamine (2nd stage of example 37) in 10 ml of pyridine and there is gradually added with agitation and at ambient temperature 0.02 mole (2.29 g) of mesyl chloride. The agitation is continued for three hours, then the reaction mixture is poured into 60 ml of iced 2 N hydrochloric solution. The expected product precipitates. It is drained, washed with water and recrystallized in ethanol. After drying it melts at 176° C.

Second stage

Preparation of (3-nitro 6-amino) phenyl, mesylaminoethylether

There is introduced 0.01 mole (3.17 g) of (3-nitro 6-acetylamino) phenylmesylaminoethylether in 10 cc of a 35% hydrochloric solution. The mixture is heated for 25 minutes in a boiling double boiler. There are added 50 ml of water. After cooling, the mesyl derivative precipitates in crystallized form. After recrystallization in ethanol and drying it melts at 164° C.

| ANALYSIS | CALCULATED FOR $C_9H_{13}N_3O_5S$ | FOUND |
|---|---|---|
| C % | 39.27 | 39.55 |
| H % | 4.76 | 4.91 |
| N % | 15.27 | 15.41 |
| S % | 11.62 | 11.46 11.49 |

EXAMPLE 39

Preparation of (3-nitro 6-amino) phenyl, carbethoxy aminoethylether

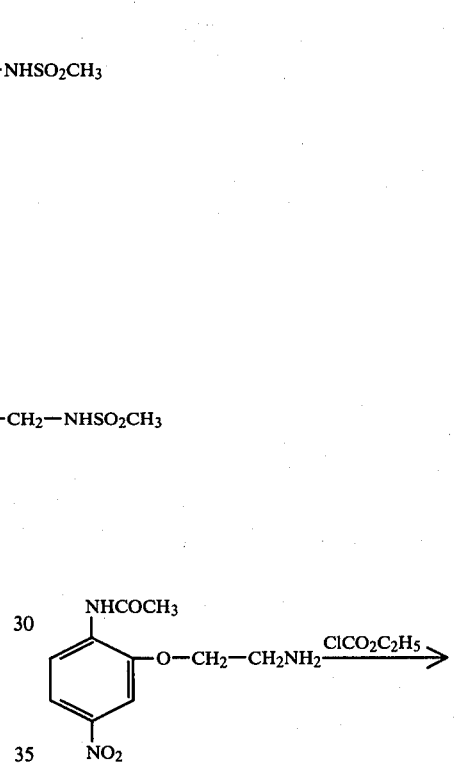

First stage

Preparation of (3-amino 6-acetylamino) phenyl, carbethoxyaminoethylether

There is introduced 0.02 mole (4.78 g) of (3-nitro 6-acetylamino) phenoxyethylamine (2nd stage of example 37) into 15 ml of dioxane. There are added 0.011 mole (1.2 g) of anhydrous sodium carbonate. The reaction mixture is heated, with agitation, in a boiling double boiler.

There is gradually added 0.022 mole (2.39 g) of ethyl chloroformate. After 4 hours of heating in the double boiler, there are again added 0.022 mole of chloroformate and 1.2 g of sodium carbonate. The heating is continued two hours then the reaction mixture, previously cooled, is poured into 60 ml of 2 N iced hydrochloric solution.

The expected product, which has precipitated in crystallized form, is drained. After washing with water and drying under a vacuum, the product is chromatographically pure and melts as 205° C.

Second stage

Preparation of (3-nitro 6-amino) phenyl, carbethoxyaminoethylether

There is dissolved 0.01 mole (3.10 g) of (3-nitro 6-acetylamino) phenyl, carbethoxyaminoethylether in 10 ml of 96% sulfuric acid. Then the reaction medium is heated for an hour at 80° C. After cooling, it is poured into 60 ml of ice water, neutralized with ammonia. The expected product precipitates first in oil form then crystallizes. After washing with water, drying and recrystallization in benzene it melts at 112° C.

| ANALYSIS | CALCULATED FOR $C_{11}H_{15}N_3O_5$ | FOUND |
|---|---|---|
| C % | 49.07 | 49.15 |
| H % | 5.62 | 5.68 |
| N % | 15.61 | 15.40 |

EXAMPLE 40

Preparation of (4-nitro 2-amino) phenyl, mesylaminoethylether

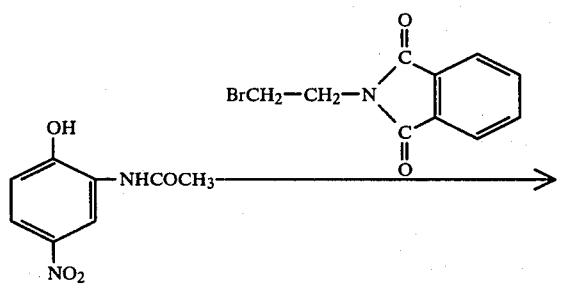

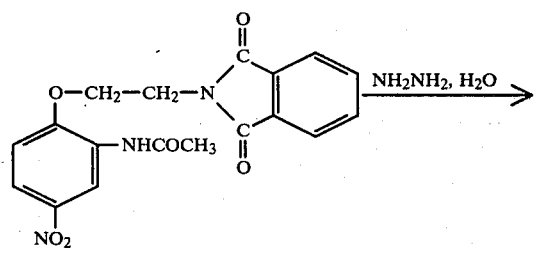

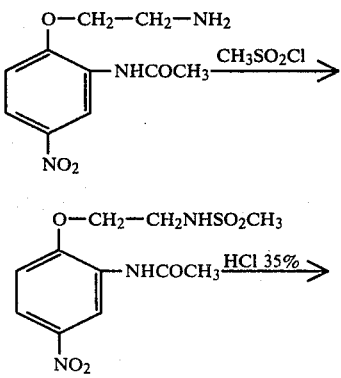

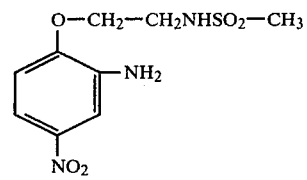

First stage

Preparation of (4-nitro 2-acetylamino) phenyl, β-phthalimidoethylether

There is dissolved 0.06 mole (11.75 g) of 4-nitro 2-acetylamino phenol in 60 ml of hexamethylphosphorotriamide (HMPT). To this solution are added 12 g of potassium carbonate and 0.066 mole (16.8 g) of β-bromoethylphthalimide. The reaction mixture is heated for 10 hours in a boiling double boiler, then poured, after cooling, into 300 ml of an iced normal sodium solution. The expected product, which has precipitated, is drained. After washing with water and drying under vacuum it melts at 224° C.

Second stage

Preparation of (4-nitro 2-acetylamino) phenoxyethylamine

There are heated for two hours in a boiling double boiler 0.018 mole (6.64 g) of (4-nitro 2-acetylamino) phenyl, β-phthalimidoethylether and 1.8 ml of 98% hydrazine hydrate in 50 ml of normal propyl alcohol. The reaction medium is cooled to 0° C. The expected product, which has precipitated in crystallized form, is drained. It is washed several times with an 0.5 N sodium solution, then with water. After recrystallization in alcohol the product melts at 158° C.

| ANALYSIS | CALCULATED FOR $C_{10}H_{13}N_3O_4$ | FOUND |
|---|---|---|
| C % | 50.20 | 50.12 |
| H % | 5.48 | 5.64 |
| N % | 17.57 | 17.34 |

Third stage

Preparation of (4-nitro 2-acetylamino) phenyl, mesylaminoethylether

There is introduced 0.22 mole (52.62 g) of (4-nitro 2-acetylamino) phenoxyethylamine in 210 ml of pyrdidine. To this suspension is added gradually with agitation and without exceeding 65° C., 0.33 mole (26 ml) of methane sulfochloride. The agitation is continued for three hours as ambient temperature, then the pyridine solution is poured into 1250 ml of iced 2 N hydrochloric solution. The expected product precipitates in crystallized form. It is drained, washed with water. After drying, it melts at 194° C.

Fourth stage

Preparation of (4-nitro 2-amino) phenyl, mesylaminoethylether

There is introduced 0.117 mole (3.7 g) of (4-nitro 2-acetylamino) phenyl, mesylaminoethylether into 110 ml of 35% hydrochloric acid. The reaction mixture is heated in a boiling double boiler for two hours. After cooling, there are added 400 ml of ice water, then ammonia at 22° Be to a pH=6. The expected product precipitates in crystallized form. It is drained, washed with water and recrystallized with isopropanol. After drying it melts at 106° C.

| ANALYSIS | CALCULATED FOR $C_9H_{13}N_3O_5S$ | FOUND |
|---|---|---|
| C % | 39.27 | 39.40 |
| H % | 4.76 | 4.94 |
| N % | 15.27 | 15.30 |
| S % | 11.62 | 11.71 11.77 |

EXAMPLE 41

Preparation of (3-nitro 4-amino) phenoxyethylamine

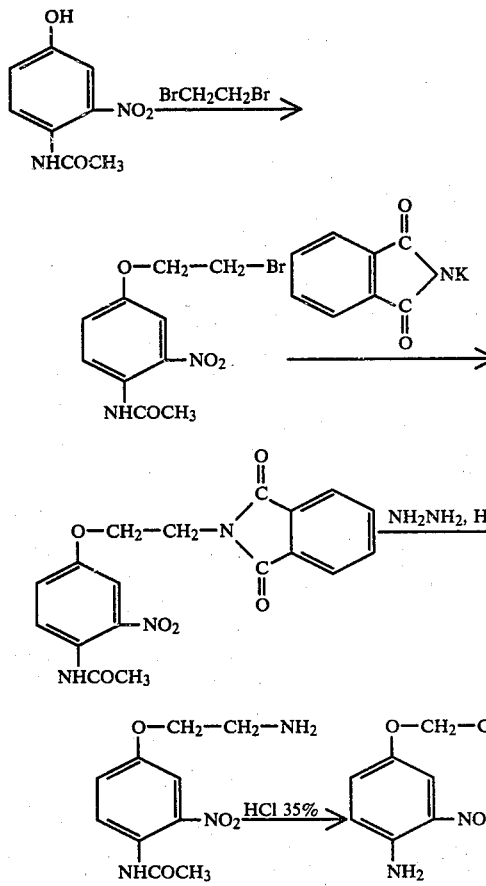

First stage

Preparation of (3-nitro 4-acetylamino) phenyl, β-bromoethylether

There is introduced 1 mole (196 g) of (3-nitro 4-acetylamino) phenol in 750 ml of hexamethylphosphorotriamide (HMPT) and 375 ml of acetone. There are added 1.5 mole (207 g) of potassium carbonate. The mixture is heated in a boiling double boiler then there are added with agitation 5 moles (445 ml) of dibromoethane. After two hours of heating in the boiling double boiler there are added 50 g of potassium carbonate and 222 ml of dibromoethane. These same additions are repeated after 4 hours and 6 hours of heating. After 12 hours of heating the reaction medium is poured onto 9 kg of ice water. The expected product first precipitates in oily form then crystallizes. It is drained, washed with water and recrystallized in a 50% water-alcohol mixture. After drying under a vacuum it melts at 116° C.

| ANALYSIS | CALCULATED FOR $C_{10}H_{11}N_2O_4Br$ | FOUND |
|---|---|---|
| C % | 39.60 | 39.65 |
| H % | 3.63 | 4.00 |
| N % | 9.24 | 9.24 |
| Br | 26.40 | 26.05 |

Second stage

Preparation of (3-nitro 4-acetylamino) phenyl, β-phthalimodoethylether

There are introduced 0.01 mole (3.03 g) of (3-nitro 4-acetylamino) phenyl, β-bromoethylether and 0.012 mole (2.22 g) of potassium phthalimide in 15 ml of dimethylformamide. The mixture is heated with agitation for 2 hours 30 minutes in a boiling double boiler. After cooling, the reaction medium is poured into 100 ml of ice water. The expected product precipitates in crystallized form, is drained, washed with water and recrystallized twice in acetic acid. After drying under vacuum it melts at 193° C.

| ANALYSIS | CALCULATED FOR $C_{18}H_{15}N_3O_6$ | FOUND |
|---|---|---|
| C % | 58.53 | 58.75 |
| H % | 4.06 | 4.30 |
| N % | 11.38 | 11.43 |

Third stage

Preparation of (3-nitro 4-acetylamino) phenoxyethylamine

There is added 0.25 mole (92.25 g) of 3-nitro 4-acetylamino) phenyl, β-phthalimidoethylether to 720 ml of normal propyl alcohol. The propanol solution is brought to reflux then there is added gradually with agitation 0.5 mole (24.2 ml) of hydrazine hydrate. When the addition is completed, the reflux is continued for 40 minutes. After cooling, there are added 120 ml of 35% hydrochloric acid. The mixture is kept at −10° C. for 30 minutes. The expected product precipitates in hydrochloride form, in mixture with phthalhydrazide hydrochloride.

This mixture of hydrochlorides is dissolved in an iced normal sodium solution. The sodium solution is extracted with chloroform. The chloroform phase is washed with a little water, dried on sodium sulfate and evaporated under vacuum. The oily residue, constituted by the expected product, has added to it a little petroleum ether. It crystallizes. It is drained, recrystallized in cyclohexane and dried under vacuum. It melts at 99° C.

| ANALYSIS | CALCULATED FOR $C_{10}H_{13}N_3O_4$ | FOUND |
|---|---|---|
| C % | 50.21 | 50.23 |
| H % | 5.44 | 5.37 |
| N % | 17.57 | 17.65 |

Fourth stage

Preparation of (3-nitro 4-amino) phenoxyethylamine

There is introduced 0.1 mole (23.9 g) of (3-nitro 4-acetylamino) phenoxyethylamine in 75 ml of 35% hydrochloric acid and 20 ml of acetic acid. After a hour of heating in the boiling double boiler with agitation, the reaction medium is cooled and the expected product, crystallized in the form of the dihydrochloride, is drained. It is drained then dissolved in 150 ml of ice water. A 4 N sodium solution is added to obtain a pH equal to 2 to obtain the expected product which precipitates in the form of orange red mono-hydrochloride which melts with decomposition at 247° C. (monohydrochloride used in example 43 below).

By treatment of this monohydrochloride with a normal sodium solution at 60° C. there is obtained (3-nitro 4-amino) phenoxyethylamine. After draining, washing with water, drying under vacuum and recrystallization in benzene the product melts at 110° C.

| ANALYSIS | CALCULATED FOR C₈H₁₁N₃O₃ | FOUND |
|---|---|---|
| C % | 48.73 | 48.86 |
| H % | 4.58 | 5.61 |
| N % | 21.32 | 21.58 |

EXAMPLE 42

Preparation of (3-nitro 4-amino) phenyl, β-acetylaminoethylether

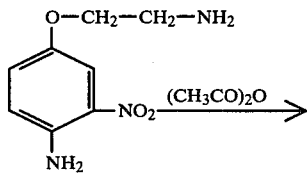

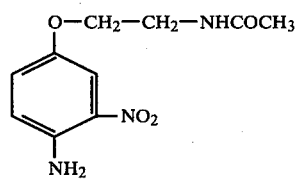

There is dissolved 0.05 mole (10 g) of (3-nitro 4-amino) phenoxyethylamine (see example 41) in 100 ml of dioxane at 50° C. To this solution is gradually added with agitation 0.052 mole (5.35 g) of acetic anhydride. With the addition finished, the temperature is kept at 50° C. for some minutes, the reaction medium is cooled then there are added 50 ml of petroleum ether. The expected product precipitates in crystallized form. It is drained and recrystallized in ethyl acetate. It melts at 133° C.

| ANALYSIS | CALCULATED FOR C₁₀H₁₃N₃O₄ | FOUND |
|---|---|---|
| C % | 50.21 | 50.05 |
| H % | 5.44 | 5.43 |
| N % | 17.57 | 17.79 |

EXAMPLE 43

Preparation of (3-nitro 4-amino) phenyl, β-ureidoethyl ether

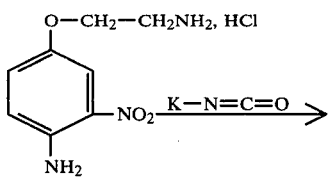

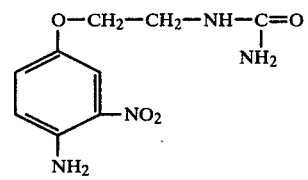

There is dissolved 0.01 mole (2.33 g) of (3-nitro 4-amino) phenoxyethylamine hydrochloride in 25 ml of water. To this solution is added at 40° C., 0.012 mole (1 g) of potassium isocyanate dissolved in 5 ml of water. The reaction medium is kept at 40° C. for 10 minutes then filtered. By cooling of the filtrate to 0° C. the expected product precipitates in crystallized form. It is drained then recrystallized in a 50% hydroacetic solution. After drying under vacuum it melts at 223° C.

| ANALYSIS | CALCULATED FOR C₉H₁₂N₄O₄ | FOUND |
|---|---|---|
| C % | 45.00 | 44.92 |
| H % | 5.00 | 5.11 |
| N % | 23.33 | 23.11 |

EXAMPLE 44

Preparation of (3-nitro 4-amino) phenyl, carbethoxyaminoethyl ether

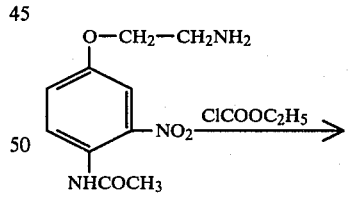

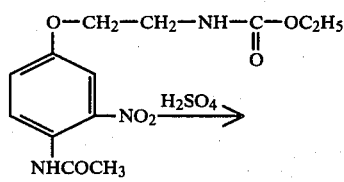

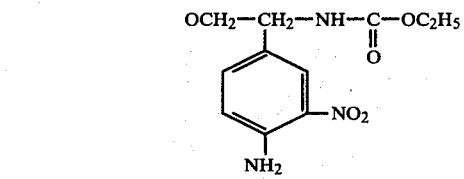

First stage

Preparation of (3-nitro 4-acetylamino) phenyl, carbethoxyaminoethyl ether

There is introduced 0.0126 mole (3 g) of (3-nitro 4-acetylamino) phenoxyethylamine (3rd stage of example 41) in 25 ml of dioxane. There are added 0.007 mole (0.7 g) of calcium carbonate then gradually with agitation 0.0138 mole (1.35 ml) of ethyl chloroformate. The agitation is continued for an hour at 35° C. The reaction medium is filtered then poured into 150 ml of iced 2 N hydrochloric solution. The expected product, which has precipitated in crystallized form, is drained, washed with water. After drying, it melts at 140° C.

Second stage

Preparation of (3-nitro 4-amino) phenyl, carbethoxyaminoethyl ether

There is introduced 0.00306 mole (0.95 g) of (3-nitro 4-acetylamino) phenyl, carbethoxyaminoethyl ether, gradually, with agitation, in 5 ml of concentrated sulfuric acid. When the dissolution is total, the sulfuric solution is kept at 75° C. for 45 minutes then poured onto 50 g of crushed ice. Ammonia is added to pH=5. The expected product precipitates in the form of an oil that rapidly crystallizes. It is drained, washed with water, and recrystallized in a benzene-cyclohexane mixture. After drying under vacuum it melts at 111° C.

| ANALYSIS | CALCULATED FOR $C_{11}H_{15}N_3O_5$ | FOUND |
|---|---|---|
| C % | 49.07 | 49.24 |
| H % | 5.57 | 4.56 |
| N % | 15.61 | 15.78 |

EXAMPLE 45

Preparation of (3-nitro 4-amino) phenyl, mesylaminoethyl ether

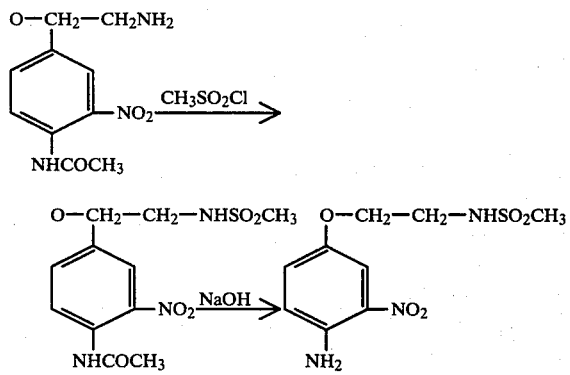

First stage

Preparation of (3-nitro 4-acetylamino) phenyl, mesylaminoethyl ether

There is introduced 0.017 mole (4 g) of (3-nitro 4-acetylamino) phenoxyethylamine prepared in the 3rd stage of example 41 in 20 ml of pyridine. To this suspension is added gradually with agitation and at ambient temperature 0.019 mole (1.47 ml) of methane sulfchloride. The reaction medium is kept at ambient temperature for an hour. The pyridine solution is then poured into 50 ml of ice water. The expected product precipitates in crystallized form. It is drained, washed with water and dried under vacuum. It melts at 140° C.

Second stage

Preparation of (3-nitro 4-amino) phenyl, mesylaminoethylether

There is dissolved 0.01 mole (3.17 g) of (3-nitro 4-acetylamino) phenyl, mesylaminoethylether in 15 ml of 2 N sodium solution. The sodium solution is kept in the boiling double boiler for 40 minutes. After cooling, 30 ml of ice water are added, then a 10 N hydrochloric solution is added to pH=7. The expected product precipitates in crystallized form. It is drained, washed with water and dried under vacuum. After recrystallization in acetic acid and drying under vacuum, the product melts at 137° C.

| ANALYSIS | CALCULATED FOR $C_9H_{13}N_3O_5S$ | FOUND |
|---|---|---|
| C % | 39.27 | 39.30 |
| H % | 4.72 | 4.80 |
| N % | 15.27 | 15.46 |
| S % | 11.63 | 11.50 |

EXAMPLE 46

Preparation of methyl, diethyl (3-nitro 4-amino) phenoxyethylammonium

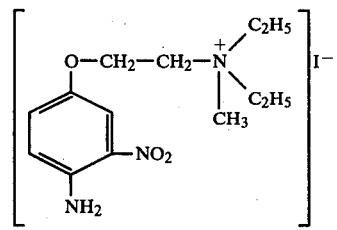

There is dissolved 0.003 mole (0.76 g) of (3-nitro 4-amino) phenyl, βN,N-diethyl aminoethyl ether (example 16) in 12 ml of benzene. There is added 0.0032 mole (0.2 ml) of methyl iodide. The reaction medium is left over night at ambient temperature. The quaternary derivative expected is drained and washed with a little benzene. It melts with decomposition at 170° C.

| ANALYSIS | CALCULATED FOR $C_{13}H_{22}N_3O_3I$ | FOUND |
|---|---|---|
| I % | 32.15 | 31.98 |

Examples of dyeing compositions containing the compounds of formula (I) are given below by way of illustrative, non-limiting example.

Examples of semi-permanent dyeing and hair setting lotions.

EXAMPLE A'

The following dye composition is prepared:

| dye of example 30 | 0.25 | g |
|---|---|---|
| butylglycol | 10 | g |
| water sufficient for | 100 | g |
| ammonia at 22° Be sufficient for | | pH = 9 |

This composition applied to bleached hair for 15 minutes at 25° C. gives it, after rinsing and shampooing, a jonquil coloring.

EXAMPLE B'

The following dye composition is prepared:

| | | |
|---|---|---|
| dye of example 45 | 0.65 | g |
| monopropyleneglycol | 7.5 | g |
| diethylene glycol monomethyl ester | 7.5 | g |
| ammonia at 22° Bé sufficient for | pH = 10 | |

This composition applied to bleached hair for 20 minutes at 35° C. gives it, after rinsing and shampooing, a golden honey coloring.

EXAMPLE C'

The following dye composition is prepared:

| | | |
|---|---|---|
| dye of example 43 | 0.1 | g |
| butylglycol | 10 | g |
| triethanolamine sufficient for | pH = 6.5 | |
| water sufficient for | 100 | g |

This dye composition applied to bleached hair for 20 minutes at 30° C. gives it, after rinsing and shampooing, a bright apricot coloring.

EXAMPLE D'

The following dye composition is prepared:

| | | |
|---|---|---|
| dye of example 44 | 0.23 | g |
| ethylglycol | 20 | g |
| butylglycol | 8 | g |
| ammonia at 22° Bé sufficient for | pH = 9 | |
| water sufficient for | 100 | g |

This dye composition applied for 20 minutes at 25° C. to bleached hair give it, after rinsing and shampooing, a topaz coloring.

EXAMPLE E'

The following dye composition is prepared:

| | | |
|---|---|---|
| dye of example 37 | 1 | g |
| sodium lauryl sulfate at 19% starting oxyethylened alcohol | 20 | g |
| TRILON B | 0.2 | g |
| ammonia at 22° Bé | 10 | g |
| water sufficient for final pH = 10.5 | 100 | g |

This dye composition applied for 10 minutes at 20° C. to bleached hair gives it a gorse coloring.

EXAMPLE F'

The following dye composition is prepared:

| | | |
|---|---|---|
| dye of example 29 | 0.2 | g |
| lauric alcohol with 10.5 mole of ethylene oxide | 10 | g |
| ammonia at 22° Bé sufficient for | pH = 8 | |
| water sufficient for | 100 | g |

This dye composition applied for 20 minutes at ambient temperature to bleached hair gives, after rinsing and shampooing, a golden sand coloring.

EXAMPLE G'

The following dye composition is prepared:

| | | |
|---|---|---|
| dye of example 41 | 0.18 | g |
| ammonium alkyl sulfate in $C_{12}$-$C_{14}$ 70% $C_{12}$ 30% $C_{14}$ | 15 | g |
| lauric alcohol with 10.5 mole ethylene oxide | 5 | g |
| ammonia at 22° Bé | 10 | g |
| water sufficient for final pH = 10 | 100 | g |

This dye composition applied for 15 minutes at 25° C. to bleached hair gives it, after rinsing and shampooing, a buttercup coloring.

EXAMPLE H'

The following dye composition is prepared:

| | | |
|---|---|---|
| dye of example 41 | 4 | g |
| ammonium alkyl sulfate in $C_{12}$ $C_{14}$ 70% $C_{12}$ 30% $C_{14}$ | 15 | g |
| lauric alcohol with 10.5 moles of ethylene oxide | 5 | g |
| ammonia at 22° Bé | 10 | g |
| water sufficient for final pH = 10 | 100 | g |

This dye composition applied for 15 minutes at 20° C. to 95% naturally white hair gives it a flamoyant orange coloring.

EXAMPLE I'

The following dye composition is prepared:

| | | |
|---|---|---|
| dye of example 32 | 0.55 | g |
| ethylglycol | 25 | g |
| diethanolamides of copra fatty acids | 7.5 | g |
| triethanolamine sufficient for | pH = 8.5 | |
| water sufficient for | 100 | g |

This dye composition applied for 15 minutes at 20° C. to bleached hair gives it, after rinsing and shampooing, a champagne coloring.

EXAMPLE J'

The following dye composition is prepared:

| | | |
|---|---|---|
| dye of example 34 | 1.3 | g |
| butylglycol | 10 | g |
| water sufficient for final pH = 5 | 100 | g |

This dye composition applied for 15 minutes at 20° C. to 95% naturally white hair gives it, after rinsing and shampooing, esterel coloring.

EXAMPLE K'

The following dye composition is prepared:

| | | |
|---|---|---|
| dye of example 42 | 0.2 | g |
| diethylene glycol monomethyl ester | 10 | g |
| ammonia at 22° Bé sufficient for | pH = 8 | |
| water sufficient for | 100 | g |

This dye composition applied for 30 minutes at 30° C. to bleached hair gives it, after rinsing and shampooing, a sunflower coloring.

EXAMPLE L'

The following dye composition is prepared:

| | | |
|---|---|---|
| dye of example 33 | 0.05 | g |
| 96° ethanol | 9 | g |
| carboxymethylcellulose | 4.5 | g |
| ammonia at 22° Bé sufficient for | pH = 9 | |
| water sufficient for | 100 | g |

This dye composition applied for 25 minutes at ambient temperature to bleached hair gives it, after rinsing and shampooing, a bright salmon coloring.

EXAMPLE M'

The following dye composition is prepared:

| | | |
|---|---|---|
| dye of example 36 | 0.25 | g |
| "Ethomeen C$_{25}$" (copra fatty amines with 15 moles of ethylene oxide) | 3 | g |
| monoethanolamine laurylether sulfate with 2 moles of ethylene oxide | 10 | g |
| 35% hydrochloric acid | 3 | g |
| water sufficient for | 100 | g | when the dissolution is total the pH is adjusted to 6 with triethanolamine.

This dye composition applied for 20 minutes at 25° C. to bleached hair gives it, after rinsing and shampooing, a pineapple coloring.

EXAMPLE N'

The following dye composition is prepared:

| | | |
|---|---|---|
| dye of example 31 | 0.5 | g |
| oleic alcohol oxyethylened with 2 moles of ethylene oxide | 3.2 | g |
| oleic alcohol oxyethylened with 4 moles of ethylene oxide | 4.8 | g |
| propylene glycol | 20 | g |
| ammonia at 22° Bé sufficient for | pH = 10 | |
| water sufficient for | 100 | g |

This dye composition applied for 25 minutes at 35° C. to bleached hair gives it, after rinsing and shampooing, a citron yellow coloring.

EXAMPLE O'

The following dye composition is prepared:

| | | |
|---|---|---|
| dye of example 38 | 0.2 | g |
| ethylglycol | 20 | g |
| diethylene glycol monomethyl ester | 8 | g |
| triethanolamine sufficient for | pH = 7 | |
| water sufficient for | 100 | g |

This dye composition applied for 20 minutes at ambient temperature to bleached hair gives it, after rinsing and shampooing, a canary yellow coloring.

EXAMPLE P'

The following dye composition is prepared:

| | | |
|---|---|---|
| dye of example 39 | 0.1 | g |
| polymer { polyvinyl pyrrolidone 30% / vinyl acetate 70% } sold under code PVP/$_{VA}$ E 335 by the Geneal Aniline and Film Corporation | 2 | g |
| ethanol | 40 | g |
| triethanolamine sufficient for | pH = 7.5 | |
| water sufficient for | 100 | g |

This dye composition applied as a setting lotion to bleached hair gives it a laburnum coloring.

EXAMPLE Q'

The following dye composition is prepared:

| | | |
|---|---|---|
| dye of example 35 | 0.4 | g |
| propylene glycol | 20 | g |
| nonylphenol with 4 moles of ethylene oxide sold under the name "Remcopal 334" by the Gerlane company | 18 | g |
| nonylphenol with 9 moles of ethylene oxide sold under the name "Remcopal 349" | 18 | g |
| ammonia at 22° Bé sufficient for | pH = 10 | |
| water sufficient for | 100 | g |

This dye composition applied for 20 minutes at ambient temperature to bleached hair gives it, after rinsing and shampooing, a champagne coloring.

EXAMPLE R'

The following dye composition is prepared:

| | | |
|---|---|---|
| dye of example 40 | 0.25 | g |
| 96° alcohol | 15 | g |
| Carbopol 934 (acrylic acid polymer with molecular weight of 2 to 3 million made by Goodrich Chemical Co.) | 3.8 | g |
| water sufficient for | 100 | g |
| lactic acid sufficient for | pH = 3 | |

The dye composition applied for 30 minutes at 30° C. to 95% naturally white hair gives it a golden straw shade.

EXAMPLE S'

The following dye composition is prepared:

| | | |
|---|---|---|
| 1-hydroxy-4-γ-aminopropylaminoanthraquinone hydrochloride | 0.4 | g |
| dye of example 37 | 0.6 | g |
| (3-nitro-4-N methylamino) phenoxyethanol | 0.3 | g |
| lauric acid with 10.5 moles of ethylene oxide | 20 | g |
| ammonia at 22° Bé sufficient for | pH = 9 | |
| water sufficient for | 100 | g |

This dye composition applied for 15 minutes at 25° C. to 95% naturally white hair gives it, after rinsing and shampooing, a bronze coloring with mordore glints.

EXAMPLE T'

The following dye composition is prepared:

| | | |
|---|---|---|
| dye of example 33 | 1.5 | g |
| 1-methylamino 4-γ-aminopropyl amino anthraquinone | 0.1 | g |
| ethyl glycol | 25 | g |
| carboxymethylcellulose | 4 | g |
| ammonia at 22° Bé sufficient for | pH = 9 | |
| water sufficient for | 100 | g |

This dye composition applied for 20 minutes at 25° C. to bleached hair gives it, after rinsing and shampooing, a steel blue gray coloring.

EXAMPLE U'

The following dye composition is prepared:

| | |
|---|---|
| dye of example 43 | 0.25 g |
| dye of example 38 | 0.30 g |
| nitroparaphenylenediamine | 0.1% |
| N—methylamine 1-γ-aminopropylamino-4-anthraquinone | 0.1% |
| ethylglycol | 25 g |
| carboxymetylcellulose | 4 g |
| ammonia sufficient for | pH = 7 |
| water sufficient for | 100 g |

This composition applied to 95% naturally white hair for 20 minutes at 30° C. gives it, after rinsing and shampooing, a silver gray coloring with eucaluptus glints.

EXAMPLE V'

The following dye composition is prepared:

| | |
|---|---|
| dye of example 30 | 0.5 g |
| 2-N—β-hydroxyethylamino 5-[4'(NN ethyl, acetylaminoethyl amino) anilino] 1,4-benzoquinone | 0.025 g |
| N—[(4'-hydroxy) phenyl] 2-methyl 5-amino benzoquinone imine | 0.05 g |
| N—[(4'-hydroxy 3'-chloro) phenyl] (4''-hydroxy 3''-chloro)2-anilino benzoquinone imine | 0.05 g |
| copolymer { polyvinylpyrrolidone 60% vinyl acetate 40% } sold under the code PVP/V₄S.630 by the General Aniline and Film Corporation | 2 g |
| isopropanol | 35 g |
| triethanolamine sufficient for | pH = 8 |
| water sufficient for | 100 g |

This dye composition applied as a setting lotion to dyed hair gives it a pink beige shade.

EXAMPLE W'

The following dye composition is prepared:

| | |
|---|---|
| dye of example 46 | 1 g |
| carboxymethylcellulose | 3.3 g |
| ammonia at 22° Bé sufficient for | pH = 10 |
| water sufficient for | 100 g |

This dye composition applied to bleached hair for 10 minutes at 25° C. gives it, after rinsing and shampooing, a powerful orange coloring.

EXAMPLES OF OXIDATION DYE

EXAMPLE X'

The following dye composition is prepared:

| | |
|---|---|
| dye of example 42 | 0.5 g |
| paratoluylene diamine dihydrochloride | 0.75 g |
| 2-methyl-5-methoxy-paraphenylene diamine dihydrochloride | 0.1 g |
| 6-hydroxy phenomorpholine | 0.2 g |
| metaaminophenol | 0.5 g |
| α-naphthol | 0.1 g |
| 3-chloro 4-amino phenol hydrochloride | 0.3 g |
| butyl glycol | 5 g |
| lauric alcohol oxyethylened with 10.5 moles of ethylene oxide ammonia at 22° Bé | 5 g |
| water sufficient for | 8 g |
| | 100 g | the final pH is equal to 10

At the time of application, there are added 70 g of 20 volume hydrogen peroxide. This dye composition applied for 20 minutes at 30° C. to bleached hair gives it, after rinsing and shampooing, a deep brown coloring with light bluish glints.

EXAMPLE Y'

The following dye composition is prepared:

| | |
|---|---|
| dye of example 41 | 0.8 g |
| (2-nitro-5-NN diethylamino) phenyl, β-carboxymethylether | 0.4 g |
| 4-(N—β-hydroxyethylamino) aniline sulfate | 0.3 g |
| 2,6-dimethyl 3-amino phenol | 0.1 g |
| 2,6-diamino pyridine | 0.05 g |
| sodium laurylsulfate with 19% starting oxyethylened alcohol | 20 g |
| Trilon B | 0.2 g |
| ammonia at 22° Be | 10 g |
| water sufficient for | 100 g |

At the time of use, 60 g of 20 volume hydrogen peroxide are added.

This dye composition applied for 25 minutes at 30° C. to 95% naturally white hair gives it, after rinsing and shampooing, a very golden light brown coloring.

EXAMPLE Z'

The following dye composition is prepared:

| | |
|---|---|
| dye of example 31 | 0.3 g |
| 1-methoxy 3-nitro 4-(N—β-hydroxyethylamino) benzene | 0.5 g |
| (3-nitro 4-amino) phenoxyethanol | 0.5 g |
| 4-(N ethyl, N carbamylethyl) amino aniline | 0.9 g |
| resorcinol | 0.5 g |
| α-naphthol | 0.2 g |
| lauric alcohol with 10.5 moles of ethylene oxide | 4.7 g |
| butylglycol | 4.7 g |
| ammonia at 22° Bé | 5 g |
| water sufficient for | 100 g |
| the final pH is equal to 10 | |

At the time of use, 60 g of 20 volume hydrogen peroxide are added.

This dye composition applied for 20 minutes at 30° C. to dyed hair gives it, after rinsing and shampooing, a coffee coloration.

EXAMPLE AA'

The following dye composition is prepared:

| | |
|---|---|
| dye of example 30 | 0.5 g |
| (3-nitro 4-amino) phenoxyethanol | 0.15 g |
| 3-methoxy 4-N—β-hydroxyethylamino aniline sulfate | 0.15 g |
| 3-methyl 4-N—β-acetylaminoethylamino aniline sulfate | 0.17 g |
| paraamino-phenol | 0.5 g |
| 2-methyl 5-N—β-hydroxyethylamino phenol | 0.2 g |
| 2-methyl 5-ureido phenol | 0.5 g |
| 4-N—methyl amino phenol sulfate | 0.1 g |
| sodium lauryl sulfate with 19% starting oxyethylened alcohol | 20 g |
| Trilon B | 10 g |
| ammonia at 22° Bé | 10 g |
| water sufficient for | 100 g |
| The final pH is equal to 10. | |

At the time of use, 40 g of 20 volume hydrogen peroxide are added.

This dye composition applied to bleached hair for 15 minutes at 25° C. gives it, after rinsing and shampooing, a golden beige coloring.

EXAMPLE BB'

The following dye composition is prepared:

| | |
|---|---|
| dye of example 33 | 0.02 g |
| dye of example 37 | 0.02 g |
| 2-methyl 4-(N ethyl, N mesylaminoethyl) amino aniline | 0.8 g |
| resorcinol | 0.15 g |
| 2-methyl 5-(N—β-hydroxyethyl amino) phenol | 0.1 g |
| sodium lauryl sulfate with 10 moles of starting oxyethylened alcohol | 20 g |
| Trilon B | 0.2 g |
| 40% sodium bisulfite solution | 1 g |
| ammonia at 22° Bé | 10 g |
| 40% sodium bisulfite solution | 1 g |
| water sufficient for | 100 g |
| The final pH is equal to 10.5. | |

At the time of use, 100 g of 20 volume hydrogen peroxide are added.

The dye composition applied for 30 minutes at 25° C. to bleached hair gives it, after rinsing and shampooing, a silver gray coloring with mauve glints.

EXAMPLE CC'

The following dye composition is prepared:

| | |
|---|---|
| dye of example 37 | 0.30 g |
| 1-methoxy 3-nitro 4-N—β-hydroxyethylamino benzene | 0.30 g |
| 2,6-dimethyl-3-methoxy paraphenylene diamine dihydrochloride | 0.20 g |
| paraaminophenol | 0.15 g |
| 2,4-diamino anisole dihydrochloride | 0.10 g |
| resorcinol | 0.15 g |
| ammonium laurylsulfate | 7 g |
| propylene glycol | 25 g |
| ammonia at 22° Bé | 5 g |
| water sufficient for | 100 g |
| The final pH is equal to 9.5. | |

At the time of use, 25 g of 20 volume hydrogen peroxide are added.

The dye composition applied during 30 minutes at 25° C. to 95% naturally white hair gives it, after rinsing and shampooing, a light auburn coloring.

EXAMPLE DD'

The following dye composition is prepared:

| | |
|---|---|
| dye of example 37 | 0.30 g |
| 1-methoxy 3-nitro 4-N β-hydroxyethylamino benzene | 0.30 g |
| 4-N—di-βhydroxyethylamino aniline sulfate | 0.20 g |
| paraaminophenol | 0.15 g |
| 2,4-diamino anisole dihydrochloride | 0.10 g |
| resorcinol | 0.15 g |
| ammonium lauryl sulfate | 7 g |
| propylene glycol | 25 g |
| ammonia at 22° Bé | 5 g |
| water sufficient for | 100 g |
| The final pH is equal to 9.5. | |

At the time of use, 25 g of 20 volume of hydrogen peroxide are added.

The dye composition applied for 20 minutes at 30° C. to bleached hair gives it, after rinsing and shampooing, a very golden light brown coloring.

EXAMPLE EE'

The following dye composition is prepared:

| | |
|---|---|
| dye of example 34 | 0.35 g |
| (3-nitro 6-N β-hydroxyethylamino) phenoxyethanol | 0.3 g |
| 3-nitro 4-N—β-hydroxyethylamino NN(methyl, hydroxyethyl) aniline | 0.5 g |
| 2,5-diamino 4-methyl phenol dihydrochloride | 0.075 g |
| ammonium lauryl sulfate | 10 g |
| ammonia sufficient for | pH = 9 |
| water sufficient for | 100 g |

This dye composition applied for 20 minutes at ambient temperature to bleached hair gives it, after rinsing and shampooing, a golden bronze coloring.

EXAMPLE FF'

The following dye composition is prepared:

| | |
|---|---|
| dye of example 33 | 0.2 g |
| 4-NN(ethyl, carbamylmethylamino) aniline | 3.1 g |
| trihydroxybenzene | 2 g |
| 96° alcohol | 30 g |
| triethanolamine sufficient for | pH = 8 |
| water sufficient for | 100 g |

This dye composition applied for 30 minutes at 25° C. to bleached hair gives it, after rinsing and shampooing, a hazel coloring.

EXAMPLE GG'

The following dye composition is prepared:

| | |
|---|---|
| dye of example 34 | 4 g |
| (3-nitro-6-amino) phenyl, β-NN diethylaminoethyl ether hydrochloride | 0.5 g |
| 2,5-diamino 4-methyl phenol dihydrochloride | 1% |
| ethylglycol | 10 g |
| ammonium alkyl sulfate in $C_{12}\ C_{14}$ 70% $C_{12}$ 30% $C_{14}$ | 13.5 g |
| ammonia at 22° Bé | 10 g |
| water sufficient for | 100 g |
| The pH is equal 50 9.5 | |

This dye composition applied for 10 minutes at ambient temperature to bleached hair gives it a light brown coloring with light mordore glints.

EXAMPLE HH'

The following dye composition is prepared:

| | |
|---|---|
| dye of example 41 | 0.15 g |
| (3-nitro-4-N—methylamino) phenoxyethanol | 0.25 g |
| 2,6-diamino-4-N,N—diethylamino phenol trihydrochloride | 0.15 g |
| 2,6-diamino hydroquinone dihydrochloride | 0.15 g |
| 44'-diamino 33'55'-tetramethyl diphenylamine | 0.20 g |
| propylene glycol | 25 g |
| diethanolamides of copra fatty acids | 7 g |
| ammonia at 22° Bé | 5 g |
| water sufficient for | 100 g |

At the time of use, 25 g of 20 volume hydrogen peroxide are added.

This dye composition applied for 25 minutes at 30° C. to bleached hair gives it an auburn coloring.

What is claimed is:

1. A process for dyeing human hair comprising applying to washed and rinsed hair an effective amount of a hair dyeing composition comprising a water-alcohol solution, having a pH between 3 and 11.5, of 0.001 to 5% by weight of at least one compound of the formula

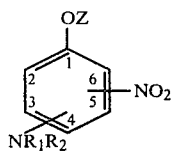

wherein
Z is lower alkyl having 1-6 carbon atoms and substituted by —OH, and
each of $R_1$ and $R_2$ is hydrogen or alkyl having 1 to 6 carbon atoms,
the —$NO_2$ substituent is in the 2, 3, 4, 5 or 6 position on the ring and the —$NR_1R_2$ substituent occupies any remaining position on the ring,
said alcohol being present in an amount from 20 to 75% by weight of the composition and being a lower alcohol having from 1 to 4 carbon atoms; said water-alcohol solution containing 1 to 3% by weight of a cosmetic resin selected from polyvinylpyrrolidone, a copolymer of crotonic acid and vinyl acetate, a copolymer of vinylpyrrolidone and vinyl acetate, a copolymer of methyl vinyl ether and maleic anhydride, a copolymer of the ethyl, isopropyl or butyl ester of maleic anhydride with methyl vinyl ether or a copolymer of maleic anhydride and butyl vinyl ether; setting the hair; and drying said hair.

2. The process of claim 1 wherein said compound is (3-nitro-4-amino) phenoxyethanol.

3. A process for dyeing human hair comprising applying to the hair an effective amount of a hair dye composition which contains in aqueous or water-alcohol solution, having a pH between 3 and 11.5, 0.001 to 5% by weight of at least one compound of the formula

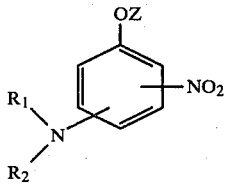

wherein
Z represents a substituted lower alkyl radical selected from the group consisting of carbalkoxyaminoalkyl, alkoxyalkyl, N,N-dialkylcarbamylalkyl, acylaminoalkyl, ureidoalkyl, mesylaminoalkyl and

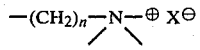

group wherein n is a whole number ranging from 1 to 6 and $X^\ominus$ is an anionic residue, and
each of $R_1$ and $R_2$ is hydrogen, lower alkyl having 1 to 6 carbon atoms or lower alkyl having 1 to 6 carbon atoms and substituted by a member selected from the group consisting of —OH, —$NH_2$, —$N(R_3)_2$, —COOH, —$CONH_2$ and —RCOOR′, wherein $R_3$ is hydrogen or lower alkyl having 1 to 6 carbon atoms and R and R′ are lower alkyl having 1 to 6 carbon atoms, the —$NO_2$ substituent is in the 2, 3, 4, 5 or 6 position on the ring and the —$NR_1R_2$ substituent occupies any remaining position on the ring, leaving said composition in contact with the hair for a period between 5 and 25 minutes, rinsing or washing the hair and thereafter drying the hair.

4. A compound selected from the group consisting of
(4-nitro-2-β-hydroxyethylamino)phenoxyethanol,
(3-nitro-6-β-hydroxyethylamino)phenoxyethanol,
(3-nitro-6-carbamylmethylamino)phenoxyethanol,
(3-nitro-6-carboxymethylamino)phenoxyethanol,
(3-nitro-6-β-diethylaminoethylamino)phenoxyethanol,
(5-nitro-2-carbamylethylamino)phenoxyethanol,
(5-nitro-2-carboxyethylamino)phenoxyethanol and
(2-nitro-4-N,N-di-β-hydroxyethylamino)phenoxyethanol.

5. The compound of claim 4 which is (4-nitro-2-β-hydroxyethylamino)phenoxyethanol.

6. The compound of claim 4 which is (3-nitro-6-β-hydroxyethylamino)phenoxyethanol.

7. The compound of claim 4 which is (3-nitro-6-carbamylmethylamino)phenoxyethanol.

8. The compound of claim 4 which is (3-nitro-6-carboxymethylamino)phenoxyethanol.

9. The compound of claim 4 which is (3-nitro-6-β-diethylaminoethylamino)phenoxyethanol.

10. The compound of claim 4 which is (5-nitro-2-carbamylethylamino)phenoxyethanol.

11. The compound of claim 4 which is (5-nitro-2-carboxyethylamino)phenoxyethanol.

12. The compound of claim 4 which is (2-nitro-4,N,N-di-β-hydroxyethylamino)phenoxyethanol.

13. A dye composition for human hair comprising an aqueous or water-alcohol solution, having a pH between 3 and 11.5, of 0.001 to 5% by weight of at least one compound selected from the group consisting of
(4-nitro-2-β-hydroxyethylamino)phenoxyethanol,
(3-nitro-6-β-hydroxyethylamino)phenoxyethanol,
(3-nitro-6-carbamylmethylamino)phenoxyethanol,
(3-nitro-6-carboxymethylamino)phenoxyethanol,
(3-nitro-6-β-diethylaminoethylamino)phenoxyethaanol,
(5-nitro-2-carbamylethylamino)phenoxyethanol,
(5-nitro-2-carboxyethylamino)phenoxyethanol and
(2-nitro-4-N,N-di-β-hydroxyethylamino)phenoxyethanol.

14. A process for dyeing human hair comprising contacting the hair with an effective amount of a composition comprising an aqueous or water-alcohol solution, having a pH between 3 and 11.5, of 0.001 to 5% by weight of a compound selected from the group consisting of
(4-nitro-2-β-hydroxyethylamino)phenoxyethanol,
(3-nitro-6-β-hydroxyethylamino)phenoxyethanol,
(3-nitro-6-carbamylmethylamino)phenoxyethanol,
(3-nitro-6-carboxymethylamino)phenoxyethanol,
(3-nitro-6-β-diethylaminoethylamino)phenoxyethanol,
(5-nitro-2-carbamylethylamino)phenoxyethanol,
(5-nitro-2-carboxyethylamino)phenoxyethanol and
(2-nitro-4-N,N-di-β-hydroxyethylamino)phenoxyethanol.

15. A process for dyeing human hair comprising applying to washed and rinsed hair an effective amount of a hair dyeing composition comprising a water-alcohol solution, having a pH between 3 and 11.5, of 0.001 to 5% by weight of at least one compound selected from the group consisting of
- (4-nitro-2-$\beta$-hydroxyethylamino)phenoxyethanol,
- (3-nitro-6-$\beta$-hydroxyethylamino)phenoxyethanol,
- (3-nitro-6-carbamylmethylamino)phenoxyethanol,
- (3-nitro-6-carboxymethylamino)phenoxyethanol,
- (3-nitro-6-$\beta$-diethylaminoethylamino)phenoxyethanol,
- (5-nitro-2-carbamylethylamino)phenoxyethanol,
- (5-nitro-2-carboxyethylamino)phenoxyethanol and
- (2-nitro-4-N,N-di-$\beta$-hydroxyethylamino)phenoxyethanol, said alcohol being present in an amount from 20 to 75% by weight of said composition and being a lower alcohol having from 1 to 4 carbon atoms; said water-alcohol solution containing 1 to 3% by weight of a cosmetic resin selected from polyvinyl pyrrolidone, a copolymer of crotonic acid and vinyl acetate, a copolymer of vinylpyrrolidone and vinyl acetate, a copolymer of methyl vinyl ether and maleic anhydride, a copolymer of the ethyl, isopropyl or butyl ester of maleic anhydride with methyl vinyl ether, or a copolymer of maleic anhydride and butyl vinyl ether, setting the hair, and drying said hair.

* * * * *